US008865729B2

(12) United States Patent
Sieger et al.

(10) Patent No.: US 8,865,729 B2
(45) Date of Patent: Oct. 21, 2014

(54) SALT FORMS OF A XANTHINE COMPOUND

(75) Inventors: Peter Sieger, Mittelbiberach (DE); Waldemar Pfrengle, Biberach an der Riss (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 160 days.

(21) Appl. No.: 13/140,853

(22) PCT Filed: Dec. 22, 2009

(86) PCT No.: PCT/EP2009/067772
§ 371 (c)(1),
(2), (4) Date: Sep. 27, 2011

(87) PCT Pub. No.: WO2010/072776
PCT Pub. Date: Jul. 1, 2010

(65) Prior Publication Data
US 2012/0129874 A1    May 24, 2012

(30) Foreign Application Priority Data

Dec. 23, 2008  (EP) .................................... 08172785

(51) Int. Cl.
*A01N 43/90* (2006.01)
*A61K 31/52* (2006.01)
*C07D 487/00* (2006.01)

(52) U.S. Cl.
USPC ...................................... 514/263.21; 544/262

(58) Field of Classification Search
None
See application file for complete search history.

(56) References Cited

U.S. PATENT DOCUMENTS

| | | |
|---|---|---|
| 2,056,046 A | 9/1936 | Fourneau |
| 2,375,138 A | 5/1945 | Salvin |
| 2,629,736 A | 2/1953 | Krimmel |
| 2,730,544 A | 1/1956 | Sahyun |
| 2,750,387 A | 6/1956 | Krimmel |
| 2,928,833 A | 3/1960 | Leake et al. |
| 3,174,901 A | 3/1965 | Sterne |
| 3,236,891 A | 2/1966 | Seemuller |
| 3,454,635 A | 7/1969 | Muth |
| 3,673,241 A | 6/1972 | Marxer |
| 3,925,357 A | 12/1975 | Okada et al. |
| 4,005,208 A | 1/1977 | Bender et al. |
| 4,061,753 A | 12/1977 | Bodor et al. |
| 4,382,091 A | 5/1983 | Benjamin et al. |
| 4,599,338 A | 7/1986 | Regnier et al. |
| 4,639,436 A | 1/1987 | Junge et al. |
| 4,687,777 A | 8/1987 | Meguro et al. |
| 4,743,450 A | 5/1988 | Harris et al. |
| 4,816,455 A | 3/1989 | Schickaneder et al. |
| 4,873,330 A | 10/1989 | Lindholm |
| 4,968,672 A | 11/1990 | Jacobson et al. |
| 5,041,448 A | 8/1991 | Janssens et al. |
| 5,051,517 A | 9/1991 | Findeisen et al. |
| 5,084,460 A | 1/1992 | Munson, Jr. et al. |
| 5,130,244 A | 7/1992 | Nishimaki et al. |
| 5,219,870 A | 6/1993 | Kim |
| 5,223,499 A | 6/1993 | Greenlee et al. |
| 5,234,897 A | 8/1993 | Findeisen et al. |
| 5,258,380 A | 11/1993 | Janssens et al. |
| 5,266,555 A | 11/1993 | Findeisen et al. |
| 5,273,995 A | 12/1993 | Roth |
| 5,284,967 A | 2/1994 | Macher |
| 5,300,298 A | 4/1994 | LaNoue |
| 5,329,025 A | 7/1994 | Wong et al. |
| 5,332,744 A | 7/1994 | Chakravarty et al. |
| 5,389,642 A | 2/1995 | Dorsch et al. |
| 5,399,578 A | 3/1995 | Buhlmayer et al. |
| 5,407,929 A | 4/1995 | Takahashi et al. |
| 5,470,579 A | 11/1995 | Bonte et al. |
| 5,591,762 A | 1/1997 | Hauel et al. |
| 5,594,003 A | 1/1997 | Hauel et al. |
| 5,602,127 A | 2/1997 | Hauel et al. |
| 5,614,519 A | 3/1997 | Hauel et al. |
| 5,719,279 A | 2/1998 | Kufner-Muhl et al. |
| 5,728,849 A | 3/1998 | Bouchard et al. |
| 5,753,635 A | 5/1998 | Buckman et al. |
| 5,830,908 A | 11/1998 | Grunenberg et al. |
| 5,879,708 A | 3/1999 | Makino et al. |
| 5,958,951 A | 9/1999 | Ahrndt et al. |
| 5,965,555 A | 10/1999 | Gebert et al. |
| 5,965,592 A | 10/1999 | Buhlmayer et al. |
| 6,011,049 A | 1/2000 | Whitcomb |
| 6,107,302 A | 8/2000 | Carter et al. |

(Continued)

FOREIGN PATENT DOCUMENTS

| | | |
|---|---|---|
| AU | 2003280680 A1 | 6/2004 |
| AU | 2009224546 A1 | 9/2009 |

(Continued)

OTHER PUBLICATIONS

International Search Report and Written Opinion for PCT/EP2009/067772 mailed Apr. 14, 2010.
Januvia; Patient Information; 2010.
Kanada, S. et al., "Safety, tolerability, pharmacokenetics and pharmacodynamics of multiple doses of BI 1356 (proposed tradename ONDERO), a dipeptidyl peptidase 4 inhibitor, in Japanese patients with type 2 diabetes" Diabetes, vol. 57, No. Suppl. 1, Jun. 2008, p. A158-A159 and 68th Annual Meeting of the American Diabetes Association: San Francisco, CA , Jun. 6-10, 2008.
Kim, D. et al., "(2R)-4-Oxo-4-(3-(Trifluoremethyl)-5,6-dihydro[1,2,4]triazolo[4,3-a]pyrazin-7(8H)-yl]-1-(2,4,5-trifluorophenyl)butan-2-amine: A Potent, Orally Active Dipeptidyl Peptidase IV inhibitor for the Treatment of Type 2 Diabetes." Journal Med. Chem, 2005, 48, p. 141-151.

(Continued)

*Primary Examiner* — Jeffrey H Murray
(74) *Attorney, Agent, or Firm* — Michael P. Morris; David L. Kershner

(57) ABSTRACT

The present invention relates to novel salt forms of 1-[(4-methyl-quinazolin-2-yl)methyl]-3-methyl-7-(2-butyn-1-yl)-8-(3-(R)-amino-piperidin-1-yl)-xanthine, a DPP-4 inhibitor and their use in pharmaceutical compositions useful in the treatment of type 2, diabetes, as well as their production.

10 Claims, 12 Drawing Sheets

(56) References Cited

U.S. PATENT DOCUMENTS

| | | |
|---|---|---|
| 6,166,063 A | 12/2000 | Villhauer |
| 6,248,758 B1 | 6/2001 | Klokkers et al. |
| 6,303,661 B1 | 10/2001 | Demuth et al. |
| 6,342,601 B1 | 1/2002 | Bantick et al. |
| 6,372,940 B1 | 4/2002 | Cavazza |
| 6,548,481 B1 | 4/2003 | Demuth et al. |
| 6,579,868 B1 | 6/2003 | Asano et al. |
| 6,727,261 B2 | 4/2004 | Gobbi et al. |
| 6,784,195 B2 | 8/2004 | Hale et al. |
| 6,821,978 B2 | 11/2004 | Chackalamannil et al. |
| 6,869,947 B2 | 3/2005 | Kanstrup et al. |
| 6,995,183 B2 | 2/2006 | Hamann et al. |
| 7,060,722 B2 | 6/2006 | Kitajima et al. |
| 7,074,794 B2 | 7/2006 | Kitajima et al. |
| 7,074,798 B2 | 7/2006 | Yoshikawa et al. |
| 7,074,923 B2 | 7/2006 | Dahanukar et al. |
| 7,109,192 B2 | 9/2006 | Hauel et al. |
| 7,179,809 B2 | 2/2007 | Eckhardt et al. |
| 7,183,280 B2 | 2/2007 | Himmelsbach et al. |
| 7,192,952 B2 | 3/2007 | Kanstrup et al. |
| 7,217,711 B2 | 5/2007 | Eckhardt et al. |
| 7,235,538 B2 | 6/2007 | Kanstrup et al. |
| 7,247,478 B2 | 7/2007 | Eberhardt et al. |
| 7,291,642 B2 | 11/2007 | Kauffmann-Hefner et al. |
| 7,361,687 B2 | 4/2008 | Barth et al. |
| 7,393,847 B2 | 7/2008 | Eckhardt et al. |
| 7,407,955 B2 | 8/2008 | Himmelsbach et al. |
| 7,407,995 B2 * | 8/2008 | Ok et al. .................. 523/205 |
| 7,432,262 B2 | 10/2008 | Eckhardt et al. |
| 7,439,370 B2 | 10/2008 | Eckhardt |
| 7,470,716 B2 | 12/2008 | Eckhardt et al. |
| 7,476,671 B2 | 1/2009 | Eckhardt et al. |
| 7,482,337 B2 | 1/2009 | Himmelsbach et al. |
| 7,495,002 B2 | 2/2009 | Langkopf et al. |
| 7,495,003 B2 | 2/2009 | Eckhardt et al. |
| 7,495,005 B2 | 2/2009 | Himmelsbach et al. |
| 7,501,426 B2 | 3/2009 | Himmelsbach et al. |
| 7,550,455 B2 | 6/2009 | Himmelsbach et al. |
| 7,560,450 B2 | 7/2009 | Eckhardt et al. |
| 7,566,707 B2 | 7/2009 | Eckhardt et al. |
| 7,569,574 B2 | 8/2009 | Maier et al. |
| 7,579,449 B2 | 8/2009 | Eckhardt et al. |
| 7,610,153 B2 | 10/2009 | Carter, Jr. et al. |
| 7,645,763 B2 | 1/2010 | Himmelsbach et al. |
| 7,718,666 B2 | 5/2010 | Boehringer et al. |
| 7,799,782 B2 | 9/2010 | Munson et al. |
| 7,820,815 B2 | 10/2010 | Pfrengle et al. |
| 7,838,529 B2 | 11/2010 | Himmelsbach et al. |
| 8,039,477 B2 | 10/2011 | Hendrix et al. |
| 8,071,583 B2 | 12/2011 | Himmelsbach |
| 8,106,060 B2 | 1/2012 | Pfrengle et al. |
| 8,119,648 B2 | 2/2012 | Himmelsbach et al. |
| 8,158,633 B2 | 4/2012 | Hendrix et al. |
| 8,178,541 B2 * | 5/2012 | Himmelsbach et al. . 514/263.21 |
| 8,232,281 B2 | 7/2012 | Dugi et al. |
| 2001/0020006 A1 | 9/2001 | Demuth et al. |
| 2001/0051646 A1 | 12/2001 | Demuth et al. |
| 2002/0019411 A1 | 2/2002 | Robl et al. |
| 2002/0137903 A1 | 9/2002 | Ellsworth et al. |
| 2002/0161001 A1 | 10/2002 | Kanstrup et al. |
| 2002/0169174 A1 | 11/2002 | Chackalamannil et al. |
| 2002/0198205 A1 | 12/2002 | Himmelsbach et al. |
| 2003/0078269 A1 | 4/2003 | Pearson et al. |
| 2003/0100563 A1 | 5/2003 | Edmondson et al. |
| 2003/0105077 A1 | 6/2003 | Kanstrup et al. |
| 2003/0114390 A1 | 6/2003 | Washburn et al. |
| 2003/0130313 A1 | 7/2003 | Fujino et al. |
| 2003/0149071 A1 | 8/2003 | Gobbi et al. |
| 2003/0166578 A1 | 9/2003 | Arch et al. |
| 2003/0199528 A1 | 10/2003 | Kanstrup et al. |
| 2003/0224043 A1 | 12/2003 | Appel et al. |
| 2003/0232987 A1 | 12/2003 | Dahanukar et al. |
| 2003/0236272 A1 | 12/2003 | Carr |
| 2004/0023981 A1 | 2/2004 | Ren et al. |
| 2004/0034014 A1 | 2/2004 | Kanstrup et al. |
| 2004/0063725 A1 | 4/2004 | Barth et al. |
| 2004/0077645 A1 | 4/2004 | Himmelsbach et al. |
| 2004/0082570 A1 | 4/2004 | Yoshikawa et al. |
| 2004/0087587 A1 | 5/2004 | Himmelsbach et al. |
| 2004/0097510 A1 | 5/2004 | Himmelsbach et al. |
| 2004/0116328 A1 | 6/2004 | Yoshikawa et al. |
| 2004/0122048 A1 | 6/2004 | Benjamin et al. |
| 2004/0122228 A1 | 6/2004 | Maier et al. |
| 2004/0126358 A1 | 7/2004 | Warne et al. |
| 2004/0138214 A1 | 7/2004 | Himmelsbach et al. |
| 2004/0138215 A1 | 7/2004 | Eckhardt et al. |
| 2004/0166125 A1 | 8/2004 | Himmelsbach et al. |
| 2004/0171836 A1 | 9/2004 | Fujino et al. |
| 2004/0180925 A1 | 9/2004 | Matsuno et al. |
| 2004/0259903 A1 | 12/2004 | Boehringer et al. |
| 2005/0020574 A1 | 1/2005 | Hauel et al. |
| 2005/0026921 A1 | 2/2005 | Eckhardt et al. |
| 2005/0032804 A1 | 2/2005 | Cypes et al. |
| 2005/0065145 A1 | 3/2005 | Cao et al. |
| 2005/0070562 A1 | 3/2005 | Jones et al. |
| 2005/0070594 A1 | 3/2005 | Kauschke et al. |
| 2005/0130985 A1 | 6/2005 | Himmelsbach et al. |
| 2005/0143377 A1 | 6/2005 | Himmelsbach et al. |
| 2005/0171093 A1 | 8/2005 | Eckhardt et al. |
| 2005/0187227 A1 | 8/2005 | Himmelsbach et al. |
| 2005/0203095 A1 | 9/2005 | Eckhardt et al. |
| 2005/0234108 A1 | 10/2005 | Himmelsbach et al. |
| 2005/0234235 A1 | 10/2005 | Eckhardt et al. |
| 2005/0239778 A1 | 10/2005 | Konetzki et al. |
| 2005/0256310 A1 | 11/2005 | Hulin et al. |
| 2005/0261271 A1 | 11/2005 | Feng et al. |
| 2005/0261352 A1 | 11/2005 | Eckhardt |
| 2005/0266080 A1 | 12/2005 | Desai et al. |
| 2005/0276794 A1 | 12/2005 | Papas et al. |
| 2006/0004074 A1 | 1/2006 | Eckhardt et al. |
| 2006/0034922 A1 | 2/2006 | Cheng et al. |
| 2006/0039974 A1 | 2/2006 | Akiyama et al. |
| 2006/0047125 A1 | 3/2006 | Leonardi et al. |
| 2006/0058323 A1 | 3/2006 | Eckhardt et al. |
| 2006/0063787 A1 | 3/2006 | Yoshikawa et al. |
| 2006/0074058 A1 | 4/2006 | Holmes et al. |
| 2006/0079541 A1 | 4/2006 | Langkopf et al. |
| 2006/0094722 A1 | 5/2006 | Yasuda et al. |
| 2006/0100199 A1 | 5/2006 | Yoshikawa et al. |
| 2006/0106035 A1 | 5/2006 | Hendrix et al. |
| 2006/0111372 A1 | 5/2006 | Hendrix et al. |
| 2006/0111379 A1 | 5/2006 | Guillemont et al. |
| 2006/0134206 A1 | 6/2006 | Iyer et al. |
| 2006/0142310 A1 | 6/2006 | Pfrengle et al. |
| 2006/0154866 A1 | 7/2006 | Chu et al. |
| 2006/0159746 A1 | 7/2006 | Troup et al. |
| 2006/0173056 A1 | 8/2006 | Kitajima et al. |
| 2006/0205711 A1 | 9/2006 | Himmelsbach et al. |
| 2006/0205943 A1 | 9/2006 | Dahanukar et al. |
| 2006/0247226 A1 | 11/2006 | Himmelsbach et al. |
| 2006/0270668 A1 | 11/2006 | Chew et al. |
| 2006/0270701 A1 | 11/2006 | Kroth et al. |
| 2007/0027168 A1 | 2/2007 | Pfrengle et al. |
| 2007/0060530 A1 | 3/2007 | Christopher et al. |
| 2007/0072803 A1 | 3/2007 | Chu et al. |
| 2007/0072810 A1 | 3/2007 | Asakawa |
| 2007/0088038 A1 | 4/2007 | Eckhardt et al. |
| 2007/0093659 A1 | 4/2007 | Bonfanti et al. |
| 2007/0142383 A1 | 6/2007 | Eckhardt et al. |
| 2007/0185091 A1 | 8/2007 | Himmelsbach et al. |
| 2007/0196472 A1 | 8/2007 | Kiel et al. |
| 2007/0197522 A1 | 8/2007 | Edwards et al. |
| 2007/0219178 A1 | 9/2007 | Muramoto |
| 2007/0259900 A1 | 11/2007 | Sieger et al. |
| 2007/0259925 A1 | 11/2007 | Boehringer et al. |
| 2007/0259927 A1 | 11/2007 | Suzuki et al. |
| 2007/0281940 A1 | 12/2007 | Dugi et al. |
| 2007/0299076 A1 | 12/2007 | Piotrowski et al. |
| 2008/0039427 A1 | 2/2008 | Ray et al. |
| 2008/0107731 A1 | 5/2008 | Kohlrausch et al. |
| 2008/0108816 A1 | 5/2008 | Zutter |
| 2008/0249089 A1 | 10/2008 | Himmelsbach et al. |
| 2008/0255159 A1 | 10/2008 | Himmelsbach et al. |
| 2008/0312243 A1 | 12/2008 | Eckhardt et al. |

(56) References Cited

U.S. PATENT DOCUMENTS

| | | |
|---|---|---|
| 2008/0318922 A1 | 12/2008 | Nakahira et al. |
| 2009/0023920 A1 | 1/2009 | Eckhardt |
| 2009/0088408 A1 | 4/2009 | Meade et al. |
| 2009/0088569 A1 | 4/2009 | Eckhardt et al. |
| 2009/0093457 A1 | 4/2009 | Himmelsbach et al. |
| 2009/0131432 A1 | 5/2009 | Himmelsbach et al. |
| 2009/0136596 A1 | 5/2009 | Munson et al. |
| 2009/0137801 A1 | 5/2009 | Himmelsbach et al. |
| 2009/0149483 A1 | 6/2009 | Nakahira et al. |
| 2009/0186086 A1 | 7/2009 | Shankar et al. |
| 2009/0192314 A1 | 7/2009 | Pfrengle et al. |
| 2009/0297470 A1 | 12/2009 | Franz |
| 2009/0301105 A1 | 12/2009 | Loerting |
| 2009/0325926 A1 | 12/2009 | Himmelsbach |
| 2010/0074950 A1 | 3/2010 | Sesha |
| 2010/0092551 A1 | 4/2010 | Nakamura et al. |
| 2010/0173916 A1 | 7/2010 | Himmelsbach et al. |
| 2010/0179191 A1 | 7/2010 | Himmelsbach et al. |
| 2010/0183531 A1 | 7/2010 | Johncock et al. |
| 2010/0204250 A1 | 8/2010 | Himmelsbach et al. |
| 2010/0209506 A1 | 8/2010 | Eisenreich |
| 2010/0310664 A1 | 12/2010 | Watson et al. |
| 2011/0009391 A1 | 1/2011 | Braun et al. |
| 2011/0046076 A1 | 2/2011 | Eickelmann et al. |
| 2011/0065731 A1 | 3/2011 | Dugi et al. |
| 2011/0092510 A1 | 4/2011 | Klein et al. |
| 2011/0098240 A1 | 4/2011 | Dugi et al. |
| 2011/0112069 A1 | 5/2011 | Himmelsbach et al. |
| 2011/0144083 A1 | 6/2011 | Himmelsbach et al. |
| 2011/0144095 A1 | 6/2011 | Himmelsbach et al. |
| 2011/0190322 A1 | 8/2011 | Klein et al. |
| 2011/0195917 A1 | 8/2011 | Dugi et al. |
| 2011/0206766 A1 | 8/2011 | Friedl et al. |
| 2011/0263493 A1 | 10/2011 | Dugi et al. |
| 2011/0263617 A1 | 10/2011 | Mark et al. |
| 2011/0275561 A1 | 11/2011 | Graefe-Mody et al. |
| 2011/0301182 A1 | 12/2011 | Dugi |
| 2012/0003313 A1 | 1/2012 | Kohlrausch et al. |
| 2012/0035158 A1 | 2/2012 | Himmelsbach et al. |
| 2012/0040982 A1 | 2/2012 | Himmelsbach et al. |
| 2012/0053173 A1 | 3/2012 | Banno et al. |
| 2012/0094894 A1 | 4/2012 | Graefe-Mody et al. |
| 2012/0107398 A1 | 5/2012 | Schneider et al. |
| 2012/0121530 A1 | 5/2012 | Klein et al. |
| 2012/0122776 A1 | 5/2012 | Graefe-Mody et al. |
| 2012/0129874 A1 | 5/2012 | Sieger et al. |
| 2012/0142712 A1 | 6/2012 | Pfrengle et al. |
| 2012/0165251 A1 | 6/2012 | Klein et al. |
| 2012/0208831 A1 | 8/2012 | Himmelsbach et al. |
| 2012/0219622 A1 | 8/2012 | Kohlrausch et al. |
| 2012/0219623 A1 | 8/2012 | Meinicke |
| 2012/0252782 A1 | 10/2012 | Himmelsbach et al. |
| 2012/0252783 A1 | 10/2012 | Himmelsbach et al. |
| 2012/0296091 A1 | 11/2012 | Sieger et al. |
| 2013/0122089 A1 | 5/2013 | Kohlrausch et al. |
| 2013/0172244 A1 | 7/2013 | Klein et al. |
| 2013/0184204 A1 | 7/2013 | Pfrengle et al. |
| 2013/0196898 A1 | 8/2013 | Dugi et al. |
| 2013/0236543 A1 | 9/2013 | Ito et al. |

FOREIGN PATENT DOCUMENTS

| | | |
|---|---|---|
| CA | 1123437 A1 | 5/1982 |
| CA | 2136288 A1 | 5/1995 |
| CA | 2418656 A1 | 2/2002 |
| CA | 2496249 A1 | 3/2004 |
| CA | 2496325 A1 | 3/2004 |
| CA | 2498423 A1 | 4/2004 |
| CA | 2505389 A1 | 5/2004 |
| CA | 2508233 A1 | 6/2004 |
| CA | 2529729 A1 | 12/2004 |
| CA | 2543074 A1 | 6/2005 |
| CA | 2555050 A1 | 9/2005 |
| CA | 2556064 A1 | 9/2005 |
| CA | 2558067 A1 | 10/2005 |
| CA | 2561210 A1 | 10/2005 |
| CA | 2562859 A1 | 11/2005 |
| CA | 2576294 A1 | 3/2006 |
| CA | 2590912 A1 | 6/2006 |
| CA | 2651019 A1 | 11/2007 |
| CA | 2651089 A1 | 11/2007 |
| CN | 101234105 A | 8/2008 |
| DE | 2205815 A1 | 8/1973 |
| DE | 2758025 A1 | 7/1979 |
| DE | 10109021 A1 | 9/2002 |
| DE | 10117803 A1 | 10/2002 |
| DE | 10238243 A1 | 3/2004 |
| DE | 102004019540 A1 | 11/2005 |
| DE | 102004024454 A1 | 12/2005 |
| DE | 102004044221 A1 | 3/2006 |
| DE | 102004054054 A1 | 5/2006 |
| EP | 0023032 A1 | 1/1981 |
| EP | 0149578 A2 | 7/1985 |
| EP | 0223403 A2 | 5/1987 |
| EP | 0237608 A1 | 9/1987 |
| EP | 0248634 A2 | 12/1987 |
| EP | 0389282 A2 | 9/1990 |
| EP | 0399285 A1 | 11/1990 |
| EP | 0400974 A2 | 12/1990 |
| EP | 409281 A1 | 1/1991 |
| EP | 0412358 A1 | 2/1991 |
| EP | 443983 A1 | 8/1991 |
| EP | 0475482 A1 | 3/1992 |
| EP | 0524482 A1 | 1/1993 |
| EP | 0657454 A1 | 6/1995 |
| EP | 0775704 A1 | 5/1997 |
| EP | 0950658 A1 | 10/1999 |
| EP | 1054012 A1 | 11/2000 |
| EP | 1066265 A1 | 1/2001 |
| EP | 1333033 | 8/2003 |
| EP | 1338595 A2 | 8/2003 |
| EP | 1406873 A2 | 4/2004 |
| EP | 1500403 A1 | 1/2005 |
| EP | 1514552 A1 | 3/2005 |
| EP | 1535906 A1 | 6/2005 |
| EP | 1537880 A1 | 6/2005 |
| EP | 1557165 A1 | 7/2005 |
| EP | 1586571 A1 | 10/2005 |
| EP | 1743655 A1 | 1/2007 |
| EP | 1760076 | 3/2007 |
| EP | 1829877 A1 | 9/2007 |
| EP | 1852108 A1 | 11/2007 |
| EP | 1897892 A2 | 3/2008 |
| EP | 2143443 A1 | 1/2010 |
| ES | 385302 A1 | 4/1973 |
| ES | 2256797 T3 | 7/2006 |
| ES | 2263057 T3 | 12/2006 |
| FR | 2707641 A1 | 1/1995 |
| GB | 2084580 A | 4/1982 |
| HU | 9003243 | 5/1990 |
| HU | 9902308 A2 | 7/2000 |
| JP | S374895 A | 6/1962 |
| JP | 770120 | 3/1995 |
| JP | 8333339 | 12/1996 |
| JP | 11193270 | 7/1999 |
| JP | 2000502684 A | 3/2000 |
| JP | 2001213770 A | 8/2001 |
| JP | 2002348279 A | 12/2002 |
| JP | 2003286287 A | 10/2003 |
| JP | 2003300977 A | 10/2003 |
| JP | 2004161749 A | 6/2004 |
| JP | 2006045156 A | 2/2006 |
| JP | 2010053576 A | 3/2010 |
| JP | 2010524580 A | 7/2010 |
| KR | 20070111099 A | 11/2007 |
| WO | 9107945 A1 | 6/1991 |
| WO | 9205175 A1 | 4/1992 |
| WO | 9219227 A2 | 11/1992 |
| WO | 9402150 A1 | 2/1994 |
| WO | 9403456 A1 | 2/1994 |
| WO | 9532178 A1 | 11/1995 |
| WO | 9609045 A1 | 3/1996 |
| WO | 9611917 A1 | 4/1996 |

(56) References Cited

FOREIGN PATENT DOCUMENTS

| | | |
|---|---|---|
| WO | 9636638 A1 | 11/1996 |
| WO | 9723447 A1 | 7/1997 |
| WO | 9723473 A1 | 7/1997 |
| WO | 9746526 A1 | 12/1997 |
| WO | 9807725 | 2/1998 |
| WO | 9811893 | 3/1998 |
| WO | 9818770 A1 | 5/1998 |
| WO | 9822464 A1 | 5/1998 |
| WO | 9828007 A1 | 7/1998 |
| WO | 9840069 A2 | 9/1998 |
| WO | 9846082 A1 | 10/1998 |
| WO | 9856406 A1 | 12/1998 |
| WO | 9929695 A1 | 6/1999 |
| WO | 9950248 A1 | 10/1999 |
| WO | 9956561 A1 | 11/1999 |
| WO | 9967279 A1 | 12/1999 |
| WO | 0073307 A2 | 12/2000 |
| WO | 0107441 A1 | 2/2001 |
| WO | 0140180 A2 | 6/2001 |
| WO | 0152825 | 7/2001 |
| WO | 0152852 A1 | 7/2001 |
| WO | 0166548 A1 | 9/2001 |
| WO | 0168646 A1 | 9/2001 |
| WO | 0172290 A2 | 10/2001 |
| WO | 0177110 A1 | 10/2001 |
| WO | 0196301 A1 | 12/2001 |
| WO | 0197808 A1 | 12/2001 |
| WO | 0202560 A2 | 1/2002 |
| WO | 0214271 A1 | 2/2002 |
| WO | 0224698 A1 | 3/2002 |
| WO | 02053516 A2 | 7/2002 |
| WO | 02068420 A1 | 9/2002 |
| WO | 03000241 A2 | 1/2003 |
| WO | 03002531 A2 | 1/2003 |
| WO | 03004496 A1 | 1/2003 |
| WO | 03024965 A2 | 3/2003 |
| WO | 03033686 A2 | 4/2003 |
| WO | 03037327 A1 | 5/2003 |
| WO | 03053929 A1 | 7/2003 |
| WO | 03055881 A1 | 7/2003 |
| WO | 03057200 A2 | 7/2003 |
| WO | 03064454 A1 | 8/2003 |
| WO | 03088900 A2 | 10/2003 |
| WO | 03094909 A2 | 11/2003 |
| WO | 03099279 A1 | 12/2003 |
| WO | 03099836 A1 | 12/2003 |
| WO | 03104229 A1 | 12/2003 |
| WO | 03106428 A1 | 12/2003 |
| WO | 2004002924 A1 | 1/2004 |
| WO | 2004011416 A1 | 2/2004 |
| WO | 2004016587 A1 | 2/2004 |
| WO | 2004018467 A2 | 3/2004 |
| WO | 2004018468 A2 | 3/2004 |
| WO | 2004018469 A1 | 3/2004 |
| WO | 2004028524 A1 | 4/2004 |
| WO | 2004033455 A1 | 4/2004 |
| WO | 2004035575 A1 | 4/2004 |
| WO | 2004041820 A1 | 5/2004 |
| WO | 2004046148 A1 | 6/2004 |
| WO | 2004048379 A1 | 6/2004 |
| WO | 2004050658 A1 | 6/2004 |
| WO | 2004052362 A1 | 6/2004 |
| WO | 2004058233 A1 | 7/2004 |
| WO | 2004062689 A1 | 7/2004 |
| WO | 2004065380 A | 8/2004 |
| WO | 2004081006 A1 | 9/2004 |
| WO | 2004082402 A1 | 9/2004 |
| WO | 2004096806 A1 | 11/2004 |
| WO | 2004096811 A1 | 11/2004 |
| WO | 2004106279 A2 | 12/2004 |
| WO | 2004108730 A1 | 12/2004 |
| WO | 2004111051 A1 | 12/2004 |
| WO | 2005000846 A1 | 1/2005 |
| WO | 2005000848 A1 | 1/2005 |
| WO | 2005007647 A1 | 1/2005 |
| WO | 2005007658 A2 | 1/2005 |
| WO | 2005012288 A1 | 2/2005 |
| WO | 2005023179 A2 | 3/2005 |
| WO | 2005049022 A2 | 6/2005 |
| WO | 2005051950 A1 | 6/2005 |
| WO | 2005058901 A1 | 6/2005 |
| WO | 2005061489 A1 | 7/2005 |
| WO | 2005063750 A1 | 7/2005 |
| WO | 2005082906 A1 | 9/2005 |
| WO | 2005085246 A1 | 9/2005 |
| WO | 2005092870 A1 | 10/2005 |
| WO | 2005092877 A1 | 10/2005 |
| WO | 2005095343 A1 | 10/2005 |
| WO | 2005095381 A1 | 10/2005 |
| WO | 2005097798 A | 10/2005 |
| WO | 2005116000 A1 | 12/2005 |
| WO | 2005116014 A1 | 12/2005 |
| WO | 2005117861 A1 | 12/2005 |
| WO | 2005117948 A1 | 12/2005 |
| WO | 2006005613 A1 | 1/2006 |
| WO | 2006027204 A1 | 3/2006 |
| WO | 2006029769 A1 | 3/2006 |
| WO | 2006036664 A1 | 4/2006 |
| WO | 2006040625 A1 | 4/2006 |
| WO | 2006047248 A1 | 5/2006 |
| WO | 2006048209 A1 | 5/2006 |
| WO | 2006048427 A1 | 5/2006 |
| WO | 2006068163 A1 | 6/2006 |
| WO | 2006071078 A1 | 7/2006 |
| WO | 2006076231 A2 | 7/2006 |
| WO | 2006083491 A2 | 8/2006 |
| WO | 2006135693 A2 | 12/2006 |
| WO | 2006137085 A1 | 12/2006 |
| WO | 2007007173 A2 | 1/2007 |
| WO | 2007014886 A1 | 2/2007 |
| WO | 2007014895 A2 | 2/2007 |
| WO | 2007017423 A1 | 2/2007 |
| WO | 2007033350 A1 | 3/2007 |
| WO | 2007035355 A2 | 3/2007 |
| WO | 2007035665 A1 | 3/2007 |
| WO | 2007041053 A2 | 4/2007 |
| WO | 2007071738 | 6/2007 |
| WO | 2007072083 A1 | 6/2007 |
| WO | 2007078726 A2 | 7/2007 |
| WO | 2007093610 A1 | 8/2007 |
| WO | 2007099345 A1 | 9/2007 |
| WO | 2007120702 A2 | 10/2007 |
| WO | 2007120936 A2 | 10/2007 |
| WO | 2007128721 A | 11/2007 |
| WO | 2007128724 A1 | 11/2007 |
| WO | 2007128761 A2 | 11/2007 |
| WO | 2007135196 A2 | 11/2007 |
| WO | 2007137107 A2 | 11/2007 |
| WO | 2007147185 A1 | 12/2007 |
| WO | 2007148185 A2 | 12/2007 |
| WO | 2007149797 A2 | 12/2007 |
| WO | 2008005569 A2 | 1/2008 |
| WO | 2008005576 A1 | 1/2008 |
| WO | 2008017670 | 2/2008 |
| WO | 2008022267 A2 | 2/2008 |
| WO | 2008055870 A1 | 5/2008 |
| WO | 2008055940 A2 | 5/2008 |
| WO | 2008070692 A2 | 6/2008 |
| WO | 2008081205 A1 | 7/2008 |
| WO | 2008083238 A2 | 7/2008 |
| WO | 2008087198 A1 | 7/2008 |
| WO | 2008093878 A1 | 8/2008 |
| WO | 2008093882 A1 | 8/2008 |
| WO | 2008113000 A1 | 9/2008 |
| WO | 2008130998 A2 | 10/2008 |
| WO | 2008131149 A2 | 10/2008 |
| WO | 2009011451 A | 1/2009 |
| WO | 2009022007 A2 | 2/2009 |
| WO | 2009022008 A1 | 2/2009 |
| WO | 2009022010 A1 | 2/2009 |
| WO | 2009024542 A2 | 2/2009 |
| WO | 2009063072 A2 | 5/2009 |
| WO | 2009099734 A1 | 8/2009 |
| WO | 2009112691 A2 | 9/2009 |

(56) References Cited

FOREIGN PATENT DOCUMENTS

| | | |
|---|---|---|
| WO | 2009121945 A2 | 10/2009 |
| WO | 2009123992 A1 | 10/2009 |
| WO | 2009147125 A1 | 12/2009 |
| WO | 2010015664 A1 | 2/2010 |
| WO | 2010018217 A2 | 2/2010 |
| WO | 2010029089 A2 | 3/2010 |
| WO | 2010043688 A1 | 4/2010 |
| WO | 2010045656 A2 | 4/2010 |
| WO | 2010072776 A1 | 7/2010 |
| WO | 2010079197 A1 | 7/2010 |
| WO | 2010086411 A1 | 8/2010 |
| WO | 2010092124 A1 | 8/2010 |
| WO | 2010092125 A1 | 8/2010 |
| WO | 2010092163 A2 | 8/2010 |
| WO | 2010096384 A2 | 8/2010 |
| WO | 2010106457 A2 | 9/2010 |
| WO | 2010147768 A1 | 12/2010 |
| WO | 2011039337 A1 | 4/2011 |
| WO | 2011039367 A2 | 4/2011 |
| WO | 2011064352 A1 | 6/2011 |
| WO | 2011113947 A1 | 9/2011 |
| WO | 2011138380 A1 | 11/2011 |
| WO | 2011138421 A1 | 11/2011 |
| WO | 2011161161 A1 | 12/2011 |
| WO | 2012031124 A2 | 3/2012 |
| WO | 2012065993 A1 | 5/2012 |
| WO | 2012106303 A1 | 8/2012 |
| WO | 2012120040 A1 | 9/2012 |
| WO | 2013098372 A1 | 7/2013 |
| WO | 2013103629 A1 | 7/2013 |

OTHER PUBLICATIONS

Korom, S. et al; Inhibition of CD26/dipeptidyl peptidase IV activity in vivo prolongs cardiac allograft survival in rat recipients1,2, Transplantation, May 27, 1997, vol. 63, No. 10, pp. 1495-1500.

Lambier, A.M. et al., Dipeptidyl-Peptidase IV from Bench to Bedside: An Update on Structural Properties, Functions, and Clinical Aspects of the Enzyme DPP IV. Critical Reviews in Clinical Laboratory Sciences, 2003, 40(3), p. 209-294.

March, J. "Advanced Organic Chemistry: Reactions, Mechanisms, and Structure". Fourth Edition, 1992, pp. 652-653.

Mendes, F.D, et al. "Recent advances in the treatment of non-alcoholic fatty liver disease". Expert Opinion on Investigational Drugs, vol. 14, No. 1, Jan. 1, 2005, p. 29-35.

Merck: "Initial Therapy with Janumet (sitagliptin/metformin) provided significantly greater blood sugar lowering compared to metformin alone in patients with type 2 diabetes". Webwire.com, Jun. 8, 2009, p. 1-4. http://www.webwire.com/ViewPressRel.asp?aId=96695.

O'Farrell, et al., "Pharmacokinetic and Pharmacodynamic Assessments of the Dipeptidyl Peptidase-4 Inhibitor PHX1149: Double-Blind, Placebo-controlled, Single-and Multiple-Dose Studies in Healthy Subjects". Clinical Therapeutics, Excerpta Medica, Princeton, NJ, vol. 29, No. 8, 2007, p. 1692-1705.

Patani George A. et al.: "Bioisoterism : A Rational Approach in Drug Design", Chemical Reviews, 1996, vol. 96, No. 8, pp. 3147-3176.

Pei, Z.: "From the bench to the bedside: Dipeptidyl peptidase IV inhibitors, a new class of oral antihyperglycemic agents" Current Opinion in Drug Discovery and Development, Current Drugs, London, GB vol. 11, No. 4, Jul. 1, 2008 pp. 512-532.

Pospisilik, et al; Dipeptidyl Peptidase IV Inhibitor Treatment Stimulates ?—Cell Survival and Islet Neogenesis in Streptozotocin-Induced Diabetic Rats; Diabetes, vol. 52, Mar. 2003 pp. 741-750.

Priimenko, B. A., et al; Synthesis and Pharmacological Activity of Derivates of 6,8-Dimethyl Imidazo(1,2-f) Xanthine—(Russ.); Khimiko-Farmatsevticheskii zhurnal (1984) vol. 18, No. 12 pp. 1456-61.

Rhee et al.: "Nitrogen-15-Labeled Deoxynucleosides. 3. Synthesis of [3-15N]-2'-Deoxyadenosine" J. Am. Chem. Soc. 1990, 112, 8174-8175.

Rosenstock, et al., "Efficacy and tolerability of initial combination therapy with vildagliptin and pioglitazone compared with component montherapy in patients with type 2 diabetes". Diabetes, Obesity and Metabolism, Mar. 2007, vol. 9, No. 2, p. 175-185.

Salomon, J., et al; Ultraviolet and g-Ray-Induced Reactions of Nucleic Acid Constituents. Reactions of Purines with Amines; Photochemistry and Photobiology (1974) vol. 19 pp. 21-27.

Sathananthan, A., et al., "Personalized pharmacotherapy for type 2 diabetes mellitus". Personalized Medicine 2009 Future Medicine Ltd, vol. 6, No. 4, Jul. 2009, p. 417-422.

Sauer, R, et al. "Water-soluble phosphate prodrugs of 1-Propargyl-7-styrylxanthine derivatives, A2A-selective adenosine receptor antagonists". Journal Med. Chem., vol. 43, Issue 3, Jan. 2000, p. 440-448.

Schwartz, M. S. et al., "Type 2 Diabetes Mellitus in Childhood: Obesity and Insulin Resistance". JAOA Review Article, vol. 108, No. 9, Sep. 2008, p. 518.

Scientific Discussion: "Eucreas. Scientific discussion". Online Oct. 2007, p. 1-27, URL:http://www.emea.europa.eu/humandocs/PDFs/EPAR/eucreas/H-807-en6.pdf. see point 2. quality aspects pp. 2-4. (EMEA).

Sedo, A. et al; "Dipeptidyl peptidase IV activity and/or structure homologs: Contributing factors in the pathogenesis of rheumatoid arthritis?" Arthritis Research & Therapy 2005, vol. 7, pp. 253-269.

Stahl, P.H., "Handbook of Pharmaceutical Salts". C.G. Wermuth, Wiley-VCH, 2002, p. 61.

Tamm, E, et al., "Double-blind study comparing the immunogenicity of a licensed DTwPHib-CRM197 conjugate vaccine (Quattvaxem TM) with three investigational, liquid formulations using lower doses of Hib-CRM197 conjugate". Science Direct, Vaccine, Feb. 2005, vol. 23, No. 14, p. 1715-1719.

Tanaka, S.. et al; "Suppression of Arthritis by the Inhibitors of Dipeptidyl Peptidase IV," In. J. Immunopharmac., vol. 19, No. 1, pp. 15-24, 1997.

Thomas, L, et al: "BI 1356, a novel and selective xanthine beased DPP-IV inhibitor, exhibits a superior profile when compared to sitagliptin and vildagliptin." Diabetologoa, vol. 50, No. Suppl. 1, Sep. 2007, p. S363.

Thomas, Leo et al: "(R)-8-(3-Amino-piperidin-1-yl)-7-but-2-ynyl-3-methyl-1-(4-methyl-quinazolin-2-ylmethyl)-3,7-dihydro-purine-2,6-dione (BI 1356), a Novel Xanthine-Based Dipeptidyl Peptidase 4 Inhibitor, Has a Superior Potency and Longer Duration of Action Compared with Other Dipeptidyl Peptidase-4 Inhibitors" Journal of Pharmacology and Experimental Therapeutics, American Socity for Therapeutics, US, vol. 325, No. 1, Apr. 1, 2008, pp. 175-182 abstract p. 177, col. 2, paragraph 1 table 1 p. 1B1, col. 2, last paragraph-p. 182, col. 1.

U.S. Appl. No. 12/724,653, filed Mar. 16, 2010—Xanthine Derivatives, the Preparation Thereof and Their Use as Pharmaceutical Compositions. Inventor: Frank Himmelsbach, et al.

U.S. Appl. No. 12/767,855, filed Apr. 27, 2010—Xanthine Derivatives, the Preparation Thereof and Their use as Pharmaceutical Compositions. Inventor: Frank Himmelsbach, et al.

Villhauer, E.B., "1-[[3-Hydroxy-1-adamantyl]amino]acetyl]-1-cyano-(S)-pyrrolidine: A Potent, Selective, and Orally Bioavailable Dipeptidyl Peptidase IV Inhibitor with Antihyperglycemic Properties" Journal Med. Chem, 2003, 46, p. 2774-2789.

Villhauer, E.B., et al., "1-{2-{5-Cyanopyridin-2-yl)amino)-ethylamino}acetyl-1-1(S)-pyrrolidine-carbonitrile: A Potent, Selective, and Orally Bioavailable Dipeptidyl Peptidase IV Inhibitor with Antihyperglycemic Properties". Journal of Medical Chemistry, 2002, vol. 45, No. 12, p. 2362-2365.

Wang Y et al: "BI-1356. Dipeptidyl-peptidase IV inhibitor, antidiabetic agent" Drugs of the Future, Prous Science, ES,vol. 33, No. 6, Jun. 1, 2008, pp. 473-477.

White, J.R., "Dipeptidyl Peptidase-IV Inhibitors: Phamacological Profile and Clinical Use". Clinical Diabetes, vol. 26, 2008, p. 53-57.

Wikipedia, Annulation. Jun. 23, 2008, http://en.wikipedia.org/wiki/Annelation.

Williams-Herman, D. et al., "Efficacy and safety of initial combination therapy with sitagliptin and metformin in patients with type 2 diabetes: a 54-week study". Current Medical Research and Opinion, Informa Healthcare, GB, vol. 25, No. 3, Jan. 2009, p. 569-583.

(56) References Cited

OTHER PUBLICATIONS

Wolff, M.E: "Burger's Medicinal Chemistry and Drug Discovery" Fifth Edition, vol. 1: Principles and Practice, pp. 975-977, 1994, John Wiley & Sons, Inc.
World Health Organization (WHO). "Addendum 1 to "The use of stems in the selection of International Nonproprietary names (INN) for pharmaceutical substances"" Online Jun. 19, 2007, pp. 1-3, retrieved from URL: http://www.who.int/medicindedocs/index/assoc/s1414e/s1414e.pdf.
X-Ray Diffraction. The United States Pharmacopeia, 2002, USP 25 NF20, p. 2088-2089.
Yasuda, et al. "E3024 3-but-2-ynyl-5-methyl-2-piperazin-1-y1-3,5-dihydro-4H-imidazol [ 4,5-d]pyridazin-4-one tosylate, is a move, selective and competitive dipeptidyl peptidase-IV inhibitor". European Journal of Pharmacology, vol. 548, No. 1-3, Oct. 24, 2006, p. 181-187. Abstract.
Yoshikawa, Seiji et al.: Chemical Abstract of Japanese Patent No. WO 2003/104229 Preparation of purinone derivatives as dipeptidylpeptidase IV (DPP-IV) inhibitors, 2003.
Zejc, Alfred, et al; "Badania Nad Piperazynowymi Pochodnymi Dwumetyloksantyn" Acta Polon Pharm, XXXV (1976) Nr. 4 pp. 417-421.
Zhong, Qing et al; "Glucose-dependent insulinotropic peptide stimulates proliferation and TGF—? release from MG-63 cells," Peptides 24 (2003) 611-616.
Zimmer et al; Synthesis of 8-Substituted Xanthines and their Oxidative Skeleton Rearrangement to 1-Oxo-2,4,7,9-tetraazaspiro[4,5]dec-2-ene-6,8,10-triones; Euripean Journal Organic Chemistry (1999) vol. 9 pp. 2419-2428.
Abstract in English for German DE2205815, 1972.
Abstract in English for German EP0023032, 1981.
Abstract in English, for KR20070111099, Nov. 11, 2007.
Ahren B: "DPP-4 inhibitors", Best practice and research in clinical endocrinology and metabolism—New therapies for diabetes 200712 GB LNKD—DOI:10.1016/J. Beem.2007.07.005, vol. 21, No. 4, Dec. 2007, pp. 517-533.
Augeri, D.J. "Discovery and Preclinical Profile of Saxagliptin (GMB-477118): A Highly Potent, Long-Acting, Orally Active Dipeptidyl Peptidase IV Inhibitor for the Treatment of Type 2 Diabetes". Journal Med. Chem, 2005, vol. 48, No. 15, p. 5025-5037.
Augusti, D.V. et al., "Quantitative determinatio of the enantiomeric composition of thalidomide solutions by electrospray ionizatio tandem mass spectrometry". Chem Comm, 2002, p. 2242-2243.
Augustyns, K. et al., The Unique Properties of Dipeptidyl-peptidase IV (DPP IV/CD 26) and the Therapeutic Potential of DPP-IV Inhibitors, Current Medicinal Chemistry, vol. 6, No. 4, 1999, pp. 311-327.
Aulinger, B.A. et al., "Ex-4 and the DPP-IV Inhibitor Vildagliptin have Additive Effects to Suppress Food Intake in Rodents". Abstract No. 1545-P, 2008.
Balaban, Y.H.et al., "Dipeptidyl peptidase IV (DDP IV) in NASH patients" Annals of Hepatology, vol. 6, No. 4, Oct. 1, 2007, pp. 242-250, abstract.
Balkan, B. et al, "Inhibition of dipeptidyl peptidase IC with NVP-DPP728 increases plasma GLP-1 (7-36 amide) concentrations and improves oral glucose tolerance in obses Zucker rates". Diabetologia, 1999, 42, p. 1324-1331.
Beljean-Leymarie et al., Hydrazines et hydrazones heterocycliques. IV. Syntheses de derives de l'hydrazine dans la serie des imidazo[4,5-d]pyridazinones-4, Can. J. Chem., vol. 61, No. 11, 1983, pp. 2563-2566.
Bollag, R.J. et al; "Osteoblast-Derived Cells Express Functional Glucose-Dependent Insulinotropic Peptide Receptors," Endocrinology, vol. 141, No. 3, 2000, pp. 1228-1235.
Brazg, R. et al: "Effect of adding sitagliptin, a dipeptidyll peptidase-4 inhibitor, to metformin on 24-h glycaemic control and beta-cell function in patients with type 2 diabetes." Diabetes, Obesity and Metabolism, Mar. 2007, vol. 9, No. 2, Mar. 2007 pp. 18-193.
Brittain, H.G., "Methods for the Characterization of Polymorphs: X-Ray Powder Diffraction," Polymorphism in Pharmaceutical Solids, 1999, p. 235-238.

Bundgaard, H. "Design of prodrugs: Bioreversible derivatives for various functional groups and chemical entities". Royal Danish School of Pharmacy, 1985, p. 1-92.
Busso et al., "Circulating CD26 is Negatively Associated with Inflammation in Human and Experimental Arthritis," Am. J. Path., vol. 166, No. 2, Feb. 2005, pp. 433-442.
Caira, M.R., "Crystalline polymorphism of organic compounds" Topics in Current Chemistry, Springer, Berlin, vol. 198, 1998, p. 163-208.
Chemical Abstract. EP412358, 1991:185517, Findeisen.
Chemical Abstract: FR2707641, 1995:543545, Dodey.
Chemical Abstracts Accession No. 106:95577 Romanenko et al., "Synthesis and Biological Activity of 3-Methyl, 7- or 8-alkyl-7,8dialkyl, heterocyclic, and cyclohexylaminoxanthines," Zaporozh. Med. Institute (1986).
Chemical Abstracts Accession No. 1987:95577: Abstract of Romanenko et al., "Synthesis and biological activity of 3-methyl, 7- or 8-alkyl, 7,8-dialkyl, heterocyclic, and cyclohexylaminoxanthines," Zapoeozh, USSR, Farmatsevtichnii Zhurnal, 1986, (Kiev), vol. 5, 1986, pp. 41-44.
Clinical Trials. "View of NCT00601250 on Jan. 25, 2008: Efficacy and Safety of BI 1356 vs Placebo added to Metformin Background Therapy in Patients with Type 2 Diabetes" Clinical Trials. Gov Archive, [Online] Jan. 25, 2008 URL:http://clinicaltrials.gov/archive/NCTO0601250/2008_01_25 [retrieved on Feb. 27, 2009].
Clinical Trials. NCT00622284. "Efficacy and safety of BI 1356 in combination with metformin in patients with type 2 diabetes" ClinicalTrials.gov (Online) No. NCT00622284, Feb. 13, 2008, p. 1-5, URL:http://clinicaltrial.gov/ct2/show/.
Clinical Trials. View of NCT00730275 updated on Aug. 7, 2008. "A study to assess the pharmacokinetics, safety and tolerability of Sitagliptin in adolescents". http://clinicaltrials.gov/archive/NCT00730275/2008_08_07.
Clinical Trials: NCT00309608. Efficacy and safety of BI 1356 in combination with metformin in patients with type2 diabetes. Boehringer Ingelheim Pharmaceuticals, Jan. 27, 2009. Clinical Trials.gov . http://clinicaltrials.gov/archive/NCT00309608/2009_01_27.
Clinical Trials: NCT00602472. "BI 1356 in combination withe metformin and a sulphonylurea in Type 2 Diabetes". DrugLib.com, Nov. 3, 2008. http://www.druglib.com/trial/08/NCT00309608.html.
Clinical Trials: NCT00622284. Efficacy and Safety of BI 1356 in Combination with Metformin in Patients with Type 2 Diabetes. Boehringer Ingelheim Pharmaceuticals, Aug. 2008. http://clinicaltrials.gov/archive/NCT00622284/2010_01_13.
Clinical Trials: NCT00798161. "Safety and efficacy of Bi 1356 Plus Metformin in Type 2 Diabetes, Factorial Design". Clinical Trials.gov archive. A Service of the U.S> National Institutes of Health. Nov. 24, 2008, p. 1-3. http://clinicaltrials.gov/archive/NCT00798161/2008_11_24.
Combs, D. W. et al., "Phosphoryl Chloride Induced Ring Contraction of 11,4-Benzodiazepinones to Chloromethylquinazolines". J. Heterocyclic Chemistry, BD. 23, 1986, p. 1263-1264.
Conarello, S.L. et al., "Mice lacking dipeptidyl peptidase IV are protected against obesity and insulin resistance". PNAS, May 27, 2003, vol. 100, No. 11, p. 6825-6830.
Cygankiewicz, Andrzej et al., Investigations into the Piperazine Derivatives of Dimethylxanthine:, Acta Polon. Pharm. [Papers of Polish Pharmacology], XXXOV, No. 5, pp. 607-612, 1977.
Dave, K.G. et al., "Reaction of Nitriles under Acidic Conditions, Part I. A General Method of Synthesis of Condensed Pyrimidines", J. Heterocyclic Chemistry, BD, 17, 1, ISSN 0022-152X,Nov. 1980, p. 1497-1500.
Deacon, C.F. et al; "Dipeptidyl peptidase IV inhabitation as an approach to the treatment and prevention of type 2 diabetes: a historical perspective;" Biochemical and Biophysical Research Communications (BBRC) 294 (2002) 1-4.
Deacon, C.F., et al. Inhibitors of dipeptidyl peptidase IV: a novel approach for the prevention and treatment of Type 2 diabetes? Expert Opinion on Investigational Drugs, Sep. 2004, vol. 13, No. 9, p. 1091-1102.
DeMeester, I. et al.; "CD26, let it cut or cut it down", Review: Immunology Today; Aug. 1999, vol. 20, No. 8 pp. 367-375.

(56) References Cited

OTHER PUBLICATIONS

Dugi, K.A. et al., "BI 1356, a novel xanthine-based DPP-IV inhibitor, exhibits high potency with a wide therapeutic window and significantly reduces postprandial glucose excursions after an oGTT". Diabetologia, vol. 50, No. Suppl 1, Sep. 2007, p. S367, and 43rd Annual Meeting of the European Association for the Study of Diabetes; Amsterdam, Netherlands, Sep. 18-21, 2007.

Eckhardt Matthias et al: 8-(3-(R)-aminopiperidin-1-yl)-7-but-2-yny 1-3-methyl-1-(4-methyl-quina zolin-2-ylmethyl)-3,7-dihydropurine-2,6-dione (BI 1356), a highly potent, selective, long-acting, and orally bioavailable DPP-4 inhibitor for the treatment of type 2 diabetes: Journal of Medicinal Chemistry, American Chemical Society. Washington.; US, vol. 50, No. 26, Dec. 1, 2007, p. 6450-6453.

Eckhardt, M. et al., "3,5-dihydro-imidazo[4,5-d]pyridazin-4-ones: a class of potent DPP-4 inhibitors" Bioorganic & Medicinal Chemistry Letters, Pergamon, Elsevier Science, GB, vol. 18, No. 11, Jun. 1, 2008, pp. 3158-3162, XP022711188.

Elrishi M a et al: "The dipeptidyl-peptidase-4 (D::-4) inhibitors: A new class of oral therapy for patients with type 2 diabetes mellitus" Practical Diabetes International Chichester, vol. 24, No. 9, Nov. 1, 2007 pp. 474-482.

Florez, Jose C., et al., "TCF7L2 Polymorphisms and progression to diabetes in the diabetes prevention program". New England Journal of Medicine, MA Medical Society, vol. 355, No. 2, Jul. 20, 2006, p. 241-250.

Gallwitz, B. et al., "Saxagliptin, a dipeptidyl peptidase IV inhibitor for the treatment of type 2 diabetes". IDrugs, vol. 11, No. 12, Dec. 2008, p. 906-917.

Garber, A.J. et al., "Update: Vildaglitin for the treatment of Type 2 diabetes" Expert Opinion on Investigational Drugs, 200801GB, vol. 17, No. 1, Jan. 2008, p. 105-113.

Garcia-Soria, et al., "The dipeptidyl peptidase-4 inhibitor PHX1149 improves blood glucose control in patents with type 2 diabetes mellitus". Diabetes, Obesity and Metabolism, Apr. 2008, vol. 10, No. 4, p. 293-300.

Gennaro, Alfonso, R; Remington: The Science and Practice of Pharmacy: Oral Solid Dosage Forms; Mack Publishing Company, Philadelphia, PA (1995) vol. II, 19th Edition, Ch. 92 pp. 1615-1649.

Giron, D.; Thermal Analysis and Calorimetric Methods in the Characterisation of Polymorphs and Solvates; Thermochimica Acta (1995) vol. 248 pp. 1-59.

Graefe-Mody et al., "The novel DPP-4 inhibitor" Diabetes, (online) 2008, XP002561421 http://professional.diabetes.org/content/posters/2008/p553-p.pdf.

Greene, T.W, et al., "Protection for the Amino Group". Protective Groups in Organic Synthesis, 3rd edition, 1999, p. 494-653.

Gwaltney, S. "Medicinal Chemistry Approaches to the Inhibition of Dipeptidyl Peptidase IV", Current Topics in Medicinal Chemistry, 2008, 8, p. 1545-1552.

He, Y.L. et al., "The influence of hepatic impairment on the pharmacokinetics f the dipeptidyl peptidase IV (DPP-4) inhibitor vildagliptin" European Journal of Clinical Pharmacology, vol. 63, No. 7, May 8, 2007, p. 677-686.

Huettner Silks et al: "BI 1356, a novel and selective xanthine based DPP-IV inhibitor, demonstrates good safety and tolerability with a wide therapeutic window" Diabetes< American Diabetes Association, US, vol. 56, No. Suppl 1, Jun. 1, 2007, p. A156.

Plummer, C.J.G. et al., "The Effect of Melting Point Distributions on DSC Melting Peaks." Polymer Bulletin, 1996, vol. 36, pp. 355-360.

Office Action for U.S. Appl. No. 10/695,597 mailed May 2, 2008.

Lakatos, P. L. et al., "Elevated Serum Dipeptidyl IV (CD26, EC 3.4.14.5) Activity in Experimental Liver Cirrhosis." European Journal of Clinical Investigation, 2000, vol. 30, No. 9, pp. 793-797.

Tribulova, N. et al. "Chronic Disturbances in NO Production Results in Histochemical and Subcellular Alterations of the Rat Heart." Physiol. Res., 2000, vol. 49, No. 1, pp. 77-88.

Schmidt, D. et al., "Fibromatosis of Infancy and Childhood Histology, Ultrastructure and Clinicopathologic Correlation." Zeitschrift für Kinderchirurgie, 1985, vol. 40, No. 1, pp. 40-46.

Edosada, C. Y. et al. "Selective Inhibition of Fibroblast Activation Protein Protease Based on Dipeptide Substrate Specificity." The Journal of Biological Chemistry, 2006, vol. 281, No. 11, pp. 7437-7444.

Hu, Y. et al., "Synthesis and Structure-activity Relationship of N-alkyl Gly-boro-Pro Inhibitors of DPP4, FAP, and DPP7." Bioorganic & Medicinal Chemistry Letters 15, 2005, pp. 4239-4242.

Charkevich, D. A., Pharmacology, M., Medicina, 1987, pp. 47-48.

Tradjenta, Highlights of Prescribing Information (revised Sep. 2012).

Inukai, T., "Treatment of Diabetes in Patients for Whom Metformin Treatment is Not Appropriate." Modern Physician, 2008, vol. 28, No. 2, pp. 163-165.

Matsumiya, T. et al., "Therapeutic Drugs for Clinicians." Diagnosis and Therapy, 2008, vol. 96, No. 2, pp. 389-390.

Hayashi, M. "Recipe for Oral Hypoglcemic Agents According to Pathological Condition." Pharmacy, 2006, vol. 57, No. 9, pp. 2735-2739.

Shintani, M. et al. "Insulin Resistance and Genes." Circulatory Science, 1997, vol. 17, No. 12, pp. 1186-1188.

Gennaro, Alfonso R., Remington Farmacia, 19th Edition, Spanish copy, 1995, p. 2470.

Berge, S. et al., "Pharmaceutical Salts." Journal of Pharmaceutical Sciences, 1977, vol. 66, No. 1, pp. 1-19.

Chemistry Review: Tradjenta, "NDA 201280, CMC Director Review Tradjenta (Linagliptin) Tablets." Center for Drug Evaluation and Research, Aug. 9, 2010, Retrieved from the internet on Nov. 1, 2013, http://www.accessdata.fda.gov/drugsatfda_docs/nda/2011/201280Orig1s000ChemR.pdf.

Nihon Ijinpo, Japan Medicinal Journal, 2001, No. 4032, p. 137.

Definition of "prevent", e-dictionary, Aug. 15, 2013, http://dictionary.reference.com/browse/prevent.

Medline Plus, "Obesity" 2013, Retrieved from internet on Aug. 22, 2013, http://www.nlm.nih.gov/medlineplus/obesity.html.

St. John Providence Health Center, "Preventing Obesity in Children and Teens." Retrieved from internet on Aug. 22, 2013, http://www.stjohnprovidence.org/Health I nfoLib/swarticle.aspx?type=85&id=P07863.

Ferry, Robert Jr., "Diabetes Causes." eMedicine Health, MedicineNet.com, 2013, Retrieved from internet on Aug. 22, 2013, http://www.onhealth.com/diabetes_health/page3.htm#diabetes_causes.

United Healthcare, "Diabetes." Retrieved from internet on Aug. 22, 2013, http://www.uhc.com/source4women/health_topics/diabetesirelatedinformation/dOf0417b073bf110VgnVCM1000002f1Ob1Oa _. htm.

Florez, J. et al. "TCF7L2 Polymorphisms and Progression to Diabetes in the Diabetes Prevention Program." The New England Journal of Medicine, 2006, vol. 355, No. 3, pp. 241-250.

Targher, G. et al., "Prevalence of Nonalcoholic Fatty Liver Disease and Its Association With Cardiovascular Disease Among Type 2 Diabetic Patients." Diabetes Care, 2007, vol. 30, No. 5, pp. 1212-1218.

Diabetesincontrol.com "EASD: Eucreas, a Combination of Galvus and Metformin, Recommended for Approval." Diabetes in Control.com, Sep. 25, 2007, Retrieved from internet on Nov. 30, 2012, http://www.diabetesincontrol.com/articles/53-diabetes-news/5145.

Ferreira, L. et al., "Effects of Sitagliptin Treatment on Dysmetabolism, Inflammation, and Oxidative Stress in an Animal Model of Type 2 Diabetes (ZDF Rat)." Mediators of Inflammation, 2010, vol. 2010, pp. 1-11.

Drucker, et al.., The incretin system:glucagon-like peptide-1 receptor agonists and dipeptidyl peptidase-4 inhibitors in type 2 diabetes. Lancet, 2006, 368: 1696-705.

Horsford, E. N. "On the source of free hydrochloric acid in the gastric juice." Proceedings of the Royal Society of London, Published in 1868-1869, vol. 17, pp. 391-395.

Halimi, et al. "Combination treatment in the management of type 2 diabetes" focus on vildagliptin and metformin as a single tablet, Vascualr Health and Risk Management, 2008, 4(3) p. 481-492.

Nielsen, L., "Incretin mimetics and DPP-IV inhibitors for the treatment of type 2 diabetes." Drug Discovery Today, 2005, vol. 10, No. 10, pp. 703-710.

(56) References Cited

OTHER PUBLICATIONS

Anstee, Quentin M., "Mouse models in non-alcoholic fatty liver disease and steatohepatitis research" (2006) International Journal of Experimental Pathology, v. 87, p. 1-16.

Sarafidis, P. et al., "Cardiometabolic Syndrome and Chronic Kidney Disease: What is the link?"JCMS 2006, 1: p. 58-65.

Kim, Kwang-Rok et al., "KR-62436, 6-{2-{2-(5-cyano4,5-dihydropyrazol-1-yl)-2-oxoethylamino}ethylamino} nicotinonitrile, is a novel dipeptidyl peptidase-IV (DDP-IV inhibitor with anti-hyperglycemic activity" European Journal of Pharmacology 518, 2005, p. 63-70.

Deacon, Carolyn F., et al., "Linagliptin, a xanthine based dipeptyl peptidase-4 inhibitor with an unusual profile for the treatment of type 2 diabetes" Expert Opinion Investig. Drugs 2010, 19 (1) p. 133-140.

Lakatos, P. L., et al., "Elevated Serum Dipeptidyl IV (CD26, EC3.4. 14.5) Activity in Experimental Liver Cirrhosis" European Journal of Clinical Investigation, 2000, V. 30, No. 9, p. 793-797.

Russell-Jones, D. et al., "Liraglutide vs insulin glargine and placebo in combination with metformin and sulfonylurea therapy in type 2 diabetes mellitus (LEAD-5 met+Su): a randomised controlled trial." Diabetologia, 2009, vol. 52, pp. 2046-2055.

Dave, Rutesh H. "Overview of pharmaceutical excipients used in tablets and capsules." Drug Topics, Oct. 24, 2008.

Abstract in English for German DE10109021, 2002.

International Search Report and Written Opinion for PCT/EP2011/054169 mailed Aug. 4, 2011.

Jones, R.M. et al., "GPR119 agonists for the treatment of type 2 diabetes". Expert Opinion on Therapeutic Patents 2009 Informa Healthcare for GBR LNKSD—DOI: 10.1517/13543770903153878, vol. 19, No. 10, Oct. 2009, p. 1339-1359.

Sune Negre, J. M. "New Galenic Contributions to Administration Forms". Continued Training for Hospital Pharmacists 3.2., (Publication date unavailable), Retrieved from internet on Feb. 23, 2011, http://www.ub.es/legmh/capitols/sunyenegre.pdf.

Clinical Trials: NCT00954447, View on Jun. 14, 2010. "Efficacy and Safety of Linagliptin in Combination with Insulin in Patients with Type 2 Diabetes". <http://clinicaltrials.gov/archive/NCT00954447/2010_06_14>.

Meece, J. "When Oral Agents Fail: Optimizing Insulin Therapy in the Older Adult". Consultant Pharmacist, The Society, Arlington, VA US. vol. 24, No. Suppl B, Jun. 1, 2009, p. 11-17.

Rosenstock, J. et al., "Alogliptin added to insulin therapy in patients with type 2 diabetes reduces HbA1c without causing weight gain or increased hypoglycaemia". Diabetes, Obesity and Metabolishm, Dec. 2009, vol. 11. No. 12, p. 1145-1152.

Thomas, L., "Chronic treatment with the Dipeptidyl Peptidase-4 Inhibitor BI 1356[9R)-8-(3-Amino-piperidin-1-yl)-7-but-2-ynyl-3-methy1-1(4-methyl-quinazolin-2-ylmethyl)-3,7-dihydro-purine-2,6-dione] Increases Basal Glucagon-Like Peptide-1 and Improves Glycemic Control in Diabetic Rodent Models" The Journal of Pharmacology and Experimental Therapeutics, Feb. 2009, vol. 328, No. 2, pp. 556-563.

Levien,T.L. et al, "New drugs in development for the treatment of diabetes", Diabetes Spectrum, American Diabetes Association, US, vol. 22, No. 2, Jan. 1, 2009, pp. 92-106.

He, Y. L. et al., "Bioequivalence of Vildagliptin/Metformin Combination Tablets and Coadministration of Vildagliptin and Metformin as Free Combination in Healthy Subjects". J. Clinical Pharmacology, 2007, vol. 47, No. 9, Abstracts of the 36th Annual Meeting of the American College of Clinical Pharmacology, San Francisco, CA, Abstract 116, p. 1210.

Bastin, R.J. et al., "Salt Selection and Optimization Procedures for Pharmaceutical New Chemical Entities". Organic Process Research and Development, 2000, vol. 4, p. 427-435.

Knorr, M. et al., "Comparison of Direct and Indirect Antioxidant Effects of Linagliptin (BI 1356, Ondero) with other Gliptins—Evidence for Anti-Inflammatory Properties of Linagliptin". Free Radical Biology and medicine, Elsevier Science, U.S. vol. 49, Oct. 23, 2010, p. S197.

International Search Report and Written Opinion for PCT/EP2010/064691 mailed Apr. 6, 2011.

Demuth, H-U. et al., "Type 2 diabetes—Therapy with dipeptidyl peptidase IV inhibitors". Biochimica et Biophysica Acta, vol. 1751(1), 2005, p. 33-44.

Hunziker, D. et al, "Inhibitors of DPP IV-recent advances and structural views", Current Topics in Medicinal Chemistry, 2005, vol. 5 issue 16, pp. 1623-1637.

Gallwitz, B. "Sitagliptin with Metformin: Profile of a Combination for the Treatment of Type 2 Diabetes". Drugs of Today, Oct. 2007, 43(10), p. 681-689.

Graefe-Mody, et al; Evaluation of the Potential for Steady-State Pharmacokinetic and Phamacodynamic Interactions Between the DPP-4 Inhibitor Linagliptin and Metformin in Healthy Subjects; Currents Medical Research and Opinion (2009) vol. 25, No. 8 pp. 1963-1972.

Conarello, S.L. et al; "Mice lacking dipeptidyl peptidase IV are protected against obesity and insulin resistance," PNAS 2003; 100:6825-6830; originally published online May 14, 2003; information current as of Dec. 2006. www.pnas.org/cgi/content/full/100/11/6825.

European Search Report for EP 08 15 9141 mailed Apr. 6, 2009 (European counterpart of U.S. Appl. No. 12/143,128).

International Search Report for PCT/EP03/12821 mailed Mar. 30, 2004.

International Search Report for PCT/EP03/13648 mailed Apr. 5, 2004.

International Search Report for PCT/EP2007/058181 mailed Nov. 28, 2007.

International Search Report and Written Opinion for PCT/EP2012/063852 mailed Sep. 6, 2012.

Uhlig-Laske, B. et al., "Linagliptin, a Potent and Selective DPP-4 Inhibitior, is Safe and Efficacious in Patients with Inadequately Controlled Type 2 Diabetes Despite Metformin Therapy". 535-P Clinical Therapeutics/New Technology—Pharmacologic Treatment of Diabetes or Its Complications, Posters, vol. 58, Jun. 5, 2009, p. A143.

International Search Report and Written Opinion for PCT/EP2011/057256 mailed Jul. 22, 2011.

Kibbe, A., Editor. Handbook of Pharmaceutical Excipients, Third Edition, Copovidon—pp. 196-197, Date of Revision: Dec. 16, 2008. Mannitol—pp. 424-425, Date of Revision: Feb. 19, 2009, Published in 2009.

Mayo Clinic Staff: "Nonalchoholic fatty liver disease: Prevention" [retrieved on Nov. 30, 2012]. retrieved from the Internet: ,URL: http://www.mayoclinic.com/health/nonalcoholic-fatty-liver-disease/DS00577DSECTION=prevention>.

Shanks, N. et al., Are animal models predictive for humans?, PEHM, Philosophy, Ethics, and Humanaities in Medicine, 4(2), 2009, 1-20.

Hermann, Robert, et al; Lack of Association of PAX4 Gene with Type 1 Diabetes in the Hungarian Populations; Diabetes (2005) vol. 54 pp. 2816-2819.

Ahren, Bo, et al; Improved Meal-Related b-Cell Function and Insulin Sensitivity by the Dipeptidyl Peptidase-IV Inhibitor Vildagliptin in Metformin-Treated Patients with Type 2 Diabetes Over 1 Year; Diabetes Care (2005) vol. 28, No. 8 pp. 1936-1940.

Brazg, Ronald, et al; Effect of Adding MK-0431 to On-Going Metforming Therapy in Type 2 Diabetic Patients Who Have Inadequate Glycemic Control on Metformin; Diabetes ADA (2005) vol. 54, Suppl. 1 p. A3.

Gallwitz, B. et al., DPP IV inhibitors for the Treatment of Type 2 Diabetes; Diabetes Frontier (2007) vol. 18, No. 6 pp. 636-642.

Garber, A. J. et al., "Effects of Vildagliptin on Glucose Control in Patients with Type 2 Diabetes Inadequately Controlled with a Sulphonylurea". Diabetes, Obesity and Metabolism (2008) vol. 10 pp. 1047-1055.

Hermansen, K., "Efficacy and Safety of the Dipeptidyl Peptidase-4 Inhibitor, Sitagliptin, in Patients with Type 2 Diabetes Mellitus Inadequately Controlled on Glimepiride Alone or on Glimepiride and Metformin". Diabetes, Obesity and Metabolism (2007) vol. 9, No. 5 pp. 733-745.

Hayashi, Michio., "Recipe for Oral Hypoglycemic Agents to Pathological Condition" Pharmacy (2006) vol. 57, No. 9 pp. 2735-2739.

(56) References Cited

OTHER PUBLICATIONS

Komori, Kiyoshi., "Treatment of Diabetes in Patients for Whom Metforming Treatment is Not Appropriate" Modern Physician (2008) vol. 27, No. 2 pp. 163-165.

Matsumiya, Teruhiko, et al., "Therapeutic Drugs for Clinicians" Diagnosis and Treatment (2008) vol. 96, No. 2 pp. 389-390.

Shintani, Maki, et al., "Insulin Resistance and Genes" Circulatory Sciences (1997) vol. 17, No. 12 pp. 1186-1188.

Kharkevich, D. A., "Educational Literature" Pharmacology (1987) Third Edition, Meditsina Press, Moscow pp. 47-48.

Herman, Gary et al. "Co-Administration of MK-0431 and Metformin in Patients with Type 2 Diabetes Does Not Alter the Pharmacokinetics of MK-0431 or Metformin" (2005) Journal of American Diabetes Association vol. 54, Supplement 1, 3 pgs.

Clinical Trial NCT00622284 (published online at clinicaltrials.gov on Feb. 22, 2008).

Anstee, Quentin M. et al. "Mouse models in non-alcholic fatty liver disease and steatohepatitis research" (2006) International Journal of Expermental Pathology, vol. 87, pp. 1-16.

Nauck, M. A. et al., "Efficacy and Safety of Adding the Dipeptidyl Peptidase-4 Inhibitor Alogliptin to Metformin Therapy in Patients with Type 2 Diabetes Inadequately Controlled with Metformin Monotherapy: A Multicentre, Randomised, Double-Blind, Placebo-Cotrolled Study." Clinical Practice, 2008, vol. 63, No. 1, pp. 46-55.

Bosi, E. et al., "Effects of Vildagliptin on Glucose Control Over 24 Weeks in Patients With Type 2 Diabetes Inadequately Controlled With Metformin." Diabetes Care, 2007, vol. 30, No. 4, pp. 890-895.

Charbonnel, B. et al., "Efficacy and Safety of the Dipeptidyl Peptidase-4 Inhibitor Sitagliptin Added to Ongoing Metformin Therapy in Patients With Type 2 Diabetes Inadequately Controlled With Metformin Alone." Diabetes Care, 2006, vol. 29, No. 12, pp. 2638-2643.

Nauck, M. A. et al., "Efficacy and Safety of the Dipeptidyl Peptidase-4 Inhibitor, Sitagliptin, Compared with the Sulfonylurea, Glipizide, in Patients with Type 2 Diabetes Inaduately Controlled on Metformin alone: A Randomized, Double-Blind, Non-Inferiority Trial." Diabetes Obesity and Metabolism, 2007, vol. 9, No. 2, pps. 194-205.

Huttner, S. et al., "Safety, Tolerability, Pharmacokinetics, and Pharmacodynamics of Single Oral Doses of BI 1356, an Inhibitor of Dipeptidyl Peptidase 4, in Healthy Male Volunteers." Journal of Clinical Pharmacology, 2008, vol. 48, No. 10, pp. 1171-1178.

Tounyoubyou, "Symposium-19: Future Perspectives on Incretion Therapy in Diabetes." 2008, vol. 51, Suppl. 1, p. S-71, S19-2.

Sarafidis, Panteleimon et al. "Cardiometabolic Syndrome and Chronic Kidney Disease: What is the Link?" JCMS (2006) 1: pp. 58-65.

Kim, Kwang-Rok et al. "KR-62436, 6-{2-[2-(5-cyano-4,5-dihydropyrazol-1-yl)-2-oxoethylamino]ethylamino} nicotinonitrile, is a novel dipeptidyl peptidase-IV (DPP-IV) inhibitor with anti-hyperglycemic activity" European Journal of Pharmacology 518 (2005) pp. 63-70.

Deacon, Carolyn F. et al. "Linaglipitn, a xanthine-based dipeptidyl peptidase-4 inhibitor with an unusual profile for the treatment of type 2 diabetes" Expert Opin. Investig. Drugs (2010) 19(1): 133-140.

Abstract in English for JP 2002/348279, Dec. 4, 2002.

Abstract in English for JP 2003/286287, Oct. 10, 2003.

Adebowale, K.O. et al., "Modification and properties of African yam bean (*Sphenostylis stenocarpa* Hochst. Ex A. Rich.) Harms starch I: Heat moisture treatments and annealing." Food Hydrocolloids, 2009, vol. 23, No. 7, pp. 1947-1957.

Alter, M. et al., "DPP-4 Inhibition on Top of Angiotensin Receptor Bockade Offers a New Therapeutic Approach for Diabetic Nephropathy." Kidney and Blood Pressue Research, 2012, vol. 36, No. 1, pp. 119-130.

American Diabetes Association, "Standards of Medical Care in Diabetes—2008." Diabetes Care, Jan. 2008, vol. 31, Supplement 1, pp. S12-S54.

Anonymous, Clinicaltrials.gov, 2008, No. NCT00622284, "Efficacy and Safety of BI 1356 in combination with metformin in patients with type 2 diabetes" p. 1-5.

Balbach, S. et al., Pharmaceutical evaluation of early development candidates "the 100 mg-approach." International Journal of Pharmaceutics, 2004, vol. 275, pp. 1-12.

Bernstein, Joel "Polymorphism in Molecular Crystals." Oxford University Press, 2002, p. 9.

Borloo, M. et al. "Dipeptidyl Peptidase IV: Development, Design, Synthesis and Biological Evaluation of Inhibitors." 1994, Universitaire Instelling Antwerpen, vol. 56, pp. 57-88.

Byrn, Stephen R. "Solid-State Chemistry of Drugs." Academic Press, 1982, pp. 1-27.

Campbell, R. Keith "Rationale for Dipeptidyl Peptidase 4 Inhibitors: A New Class of Oral Agents for the Treatment of Type 2 Diabetes Mellitus." The Annals of Pharmacotherapy, Jan. 2007, vol. 41, pp. 51-60.

Chan, J.C. et al., "Safety and efficacy of sitagliptin in patients with type 2 diabetes and chronic renal insufficiency." 2008, Diabetes, Obesity and Metabolism, vol. 10, pp. 545-555.

Chaykovska, L. et al., "Effects of DPP-4 Inhibitors on the Heart in a Rat Model of Uremic Cardiomyopathy." www.plosone.org, 2011, vol. 6, No. 11, p. e27861.

Chemical Abstracts Service, Database Accession number No. RN 668270-12-01, 2004, "1H-Purine-2,6,dione, 8-[(3R)-3-amino-1-piperidinyl]-7-(2-butyn-1-yl)-3,7-diydro-3-methyl-1-[(4-methyl-2-quinazolinyl)methyl]".

Diabetes Health Center, "Diabetic Retinopathy—Prevention." Retrieved online Mar. 22, 2011. www.diabetes.webmd.com/tc/diabetic-retinopathy-prevention <http://www.diabetes.webmd.com/tc/diabetic-retinopathy-prevention?print=true>.

Diabetic Neuropathy, Retrieved online Mar. 6, 2012. www.mayoclinic.com/health/diabetic-neuropathy/DS01045/METHOD=print&DSE <http://www.mayoclinic.com/health/diabetic-neuropathy/DS01045/METHOD=print&DSE>.

Dunitz, J. et al., "Disappearing Polymorphs." Acc. Chem. Res. 1995, vol. 28, No. 4, pp. 193-200.

eMedicine Health, "Diabetes Causes." Retrieved from internet on Aug. 22, 2013. <http://www.onhealth.com/diabetes_health/page3.htm#diabetes_causes>.

Eucreas Scientific Discussion, 2007, p. 1-27, www.emea.europa.eu/humandocs/PD/Fs/EPAR/eucreas/H-807-en6.pdf, Anonymous.

Forst, T. et al., "The Novel, Potent, and Selective DPP-4 Inhibitor BI 1356 Significantly Lowers HbA1c after only 4 weeks of Treatment in Patients with Type 2 Diabetes." Diabetes, Jun. 2007, Poster No. 0594P.

Fukushima et al., Drug for Treating Type II Diabetes (6), "action-mechanism of DPP-IV inhibitor and the availability thereof" Mebio, 2009, vol. 26, No. 8, p. 50-58.

Graefe-Mody, U. et al., "Effect of Renal Impairment on the Pharmacokinetics of the Dipeptidyl Peptidase-4 Inhibitor Linagliptin." Diabetes, Obesity and Metabolism, 2011, pp. 939-946.

Groop, P.-H. et al., "Effects of the DPP-4 Inhibitor Linagliptin on Albuminuria in Patients with Type 2 Diabetes and Diabetic Nephropathy." 48th EASD Annual Meeting, Berlin, Abstract 36, Oct. 2012, URL:http://www.abstractsonline.com/Plan/ViewAbstract.aspx?sKey=8b8817b9-ge98-4695-b9af-b6878e96a921&cKey=421edb9c-b948-48f8-b2.

Hansen, H. et al., "Co-Administration of the DPP-4 Inhibitor Linagliptin and Native GLP-1 Induced Body Weight Loss and Appetite Suppression." 73rd Annual Meeting Science Session, ADA, Chicago, Jun. 21, 2013.

Headland, K. et al., "The Effect of Combination Linagliptin and Voglibose on Glucose Control and Body Weight." 73rd Annual Meeting Science Session, ADA, Chicago, Jun. 21, 2013.

Heihachiro, A. et al., "Synthesis of Prolyl Endopeptidase Inhibitors and Evaluation of Their Structure-Activity Relationships: In Vitro Inhibition of Prolyl Endopeptidase from Canine Brain." 1993, Chemical and Pharmaceutical Bulletin, vol. 41, pp. 1583-1588.

Heise, T. et al., "Treatment with BI 1356, a Novel and Potent DPP-IV Inhibitor, Significantly Reduces Glucose Excursions after and oGTT in Patients with Type 2 Diabetes." A Journal of the American Diabetes Association, Jun. 2007, vol. 56, Supplement 1, Poster No. 0588P.

(56) References Cited

OTHER PUBLICATIONS

Herman, G. A. et al., "Dipeptidyl Peptidase-4 Inhibitors for the Treatment of Type 2 Diabetes: Focus on Sitagliptin." Clinical Pharmacology and Therapeutics, 2007, vol. 81, No. 5, pp. 761-767.

Hilficker, R. et al., "Relevance of Solid-state Properties for Pharmaceutical Products." Polymorphism in the Pharmaceutical Industry, 2006, Chapter 1, pp. 1-19.

Johansen, O.E. et al., "b-cell Function in Latnet Autoimmune Diabetes in Adults (LADA) Treated with Linagliptin Versus Glimepiride: Exploratory Results from a Two Year Double-Blind, Randomized, Controlled Study." www.abstractsonline.com, Jun. 10, 2012, XP-002708003.

Kidney Disease (Nephropathy), Retrieved online May 13, 2013, www.diabetes.org/living-with-diabetes/complications/kidney-disease-nephropathy.html <www.diabetes.org/living-with-diabetes/complications/kidney-disease-nephropathy.html>.

Kroller-Schön, S. et al., "Glucose-independent Improvement of Vascular Dysfunction in Experimental Sepsis by Dipeptidyl Peptidase-4 Inhibition." Cardiovascular Research, 2012, vol. 96, No. 1, pp. 140-149.

Lovshin, J.A. et al., "Incretin-based therapies for type 2 diabetes mellitus." Nature Reviews Endocrinology, 2009, vol. 5, pp. 262-269.

Nathan, D. et al., "Management of Hyperglycemia in Type 2 Diabetes: A Consensus Algorithm for the Initiation and Adjustment of Therapy." Diabetes Care, Aug. 2006, vol. 29, No. 8, pp. 1963-1972.

Nielsen, L., "Incretin Mimetics and DPP-IV Inhibitors for the Treatment of Type 2 Diabetes." DDT, 2005, vol. 10, No. 10, pp. 703-710.

Pratley, R. et al., "Inhibition of DPP-4: a new therapeutic approach for the treatment of type 2 diabetes." Current Medical Research and Opinion, 2007, vol. 23, No. 4, pp. 919-931.

Rosenstock, et al., Sitagliptin Study 019 Groups, Efficacy and safety of the dipeptidyl peptidase-4 inhibitor sitagliptin, Clinical Therepeutics, 2006, vol. 28, Issue 10, p. 1556-1568.

Sharkovska, Y., et al., "DPP-4 Inhibition with Linagliptin Delays the Progression of Diabetic Nephropathy in db/db Mice." 48th EASD Annual Meeting, Berlin, Abstract 35, Oct. 2012, URL:http://www.abstractsonline.com/Plan/ViewAbstract.aspx?sKey=Ob0017b9-ge90-4695-b9af-b6870e96a921&cKey=8eff47ae-db49-4c36-al42-848ac038c405&mKey=(2DBFCAF7-1539-42D5-8.

Singhal, D. et al., "Drug polymorphism and dosage form design: a practical perspective." Advanced Drug Delivery Reviews, 2004, vol. 56, pp. 335-347.

Third Party Observation for application No. EP20070728655, May 13, 2013.

Tsujihata, et al., "TAK-875, an orally available G protein-Coupled receptor 40/Free fatty acid receptor 1 Agonist, Enhances Glucose Dependent Insulin Secretion and improves both Postprandial and Fasting hyperglycemic in type 2 Diabetic rats", J. Pharm Exp. 2011, vol. 339, No. 1, p. 228-237.

Tsuprykov, O. et al., Linagliptin is as Efficacious Telmisartan in Preventing Renal Disease Progression in Rats with 5/6 Nephrectomy, 73rd Annual Meeting Science Session, ADA, Chicago, Jun. 2013 URL:http://wwww.abstractsonline.com/Plan/ViewAbstract.aspx?sKey=e68ac573-fe45-4c2f-9485-6278854fc18b&cKey=3c387569-84de-4f8c-b8.

\* cited by examiner

XRPD – diagram of the benzoate salt of BI 1356

XRPD – diagram of the tosylate salt of BI 1356

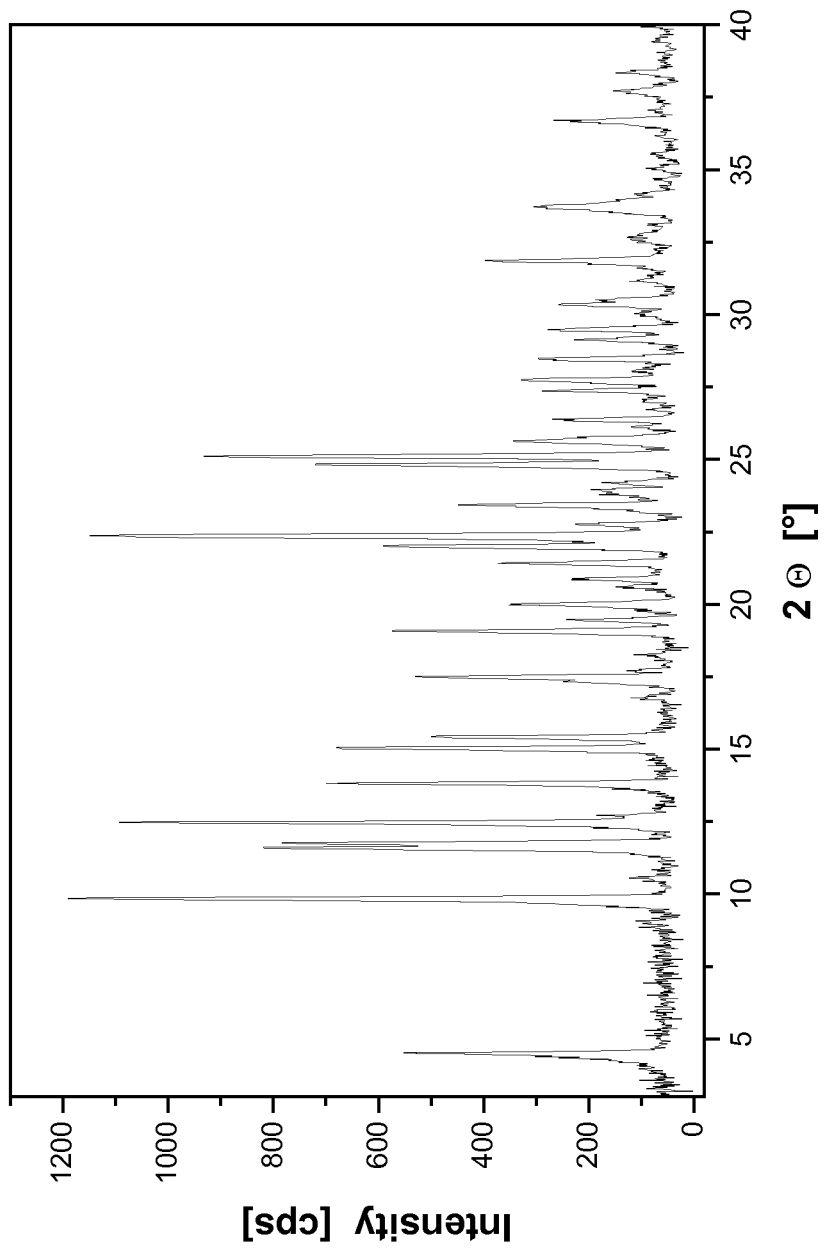

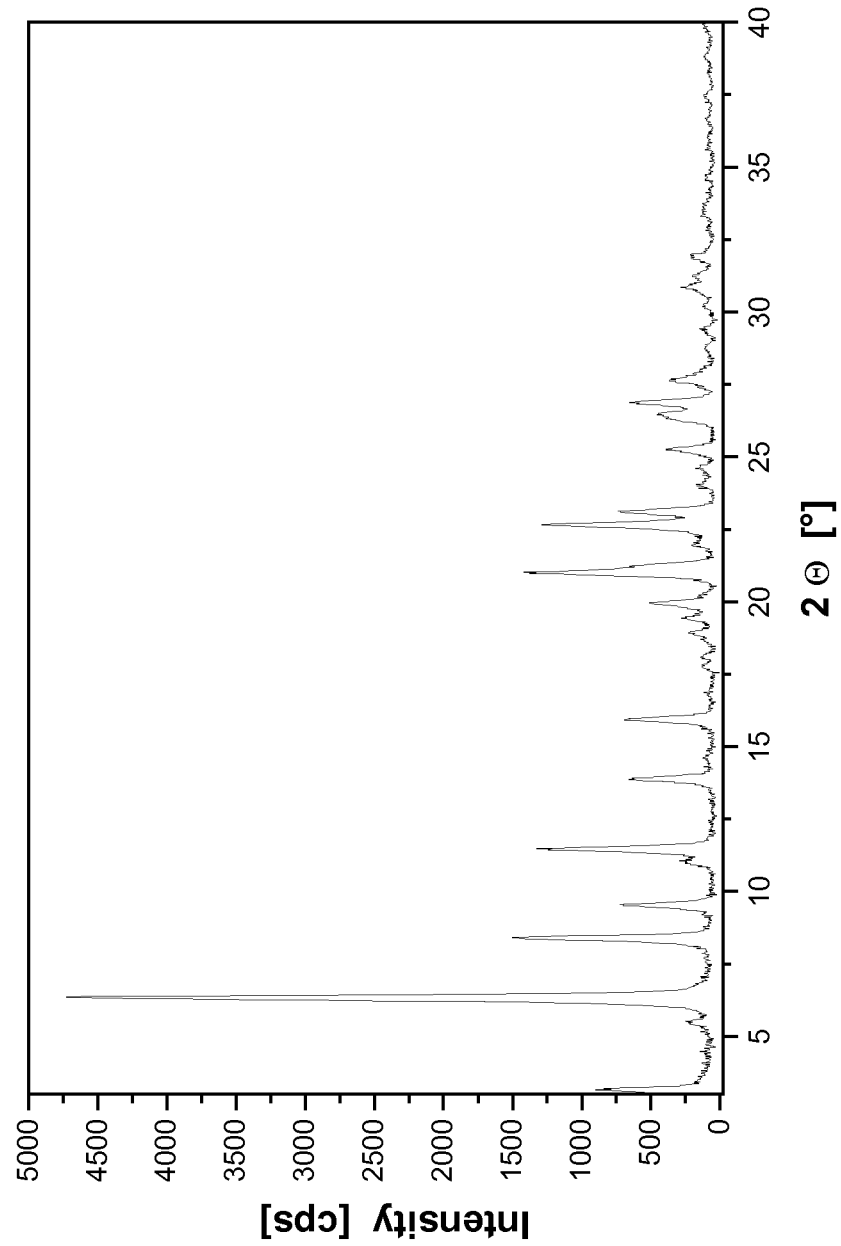

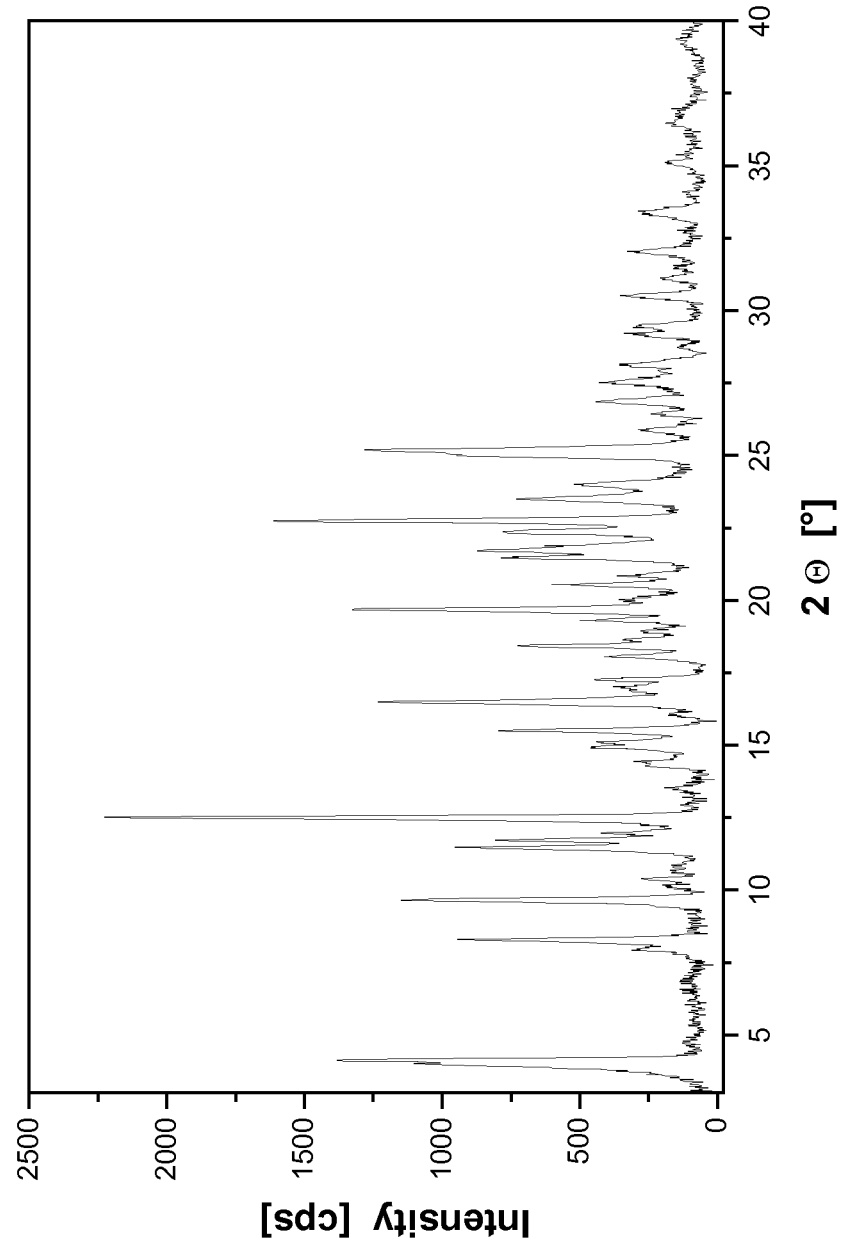

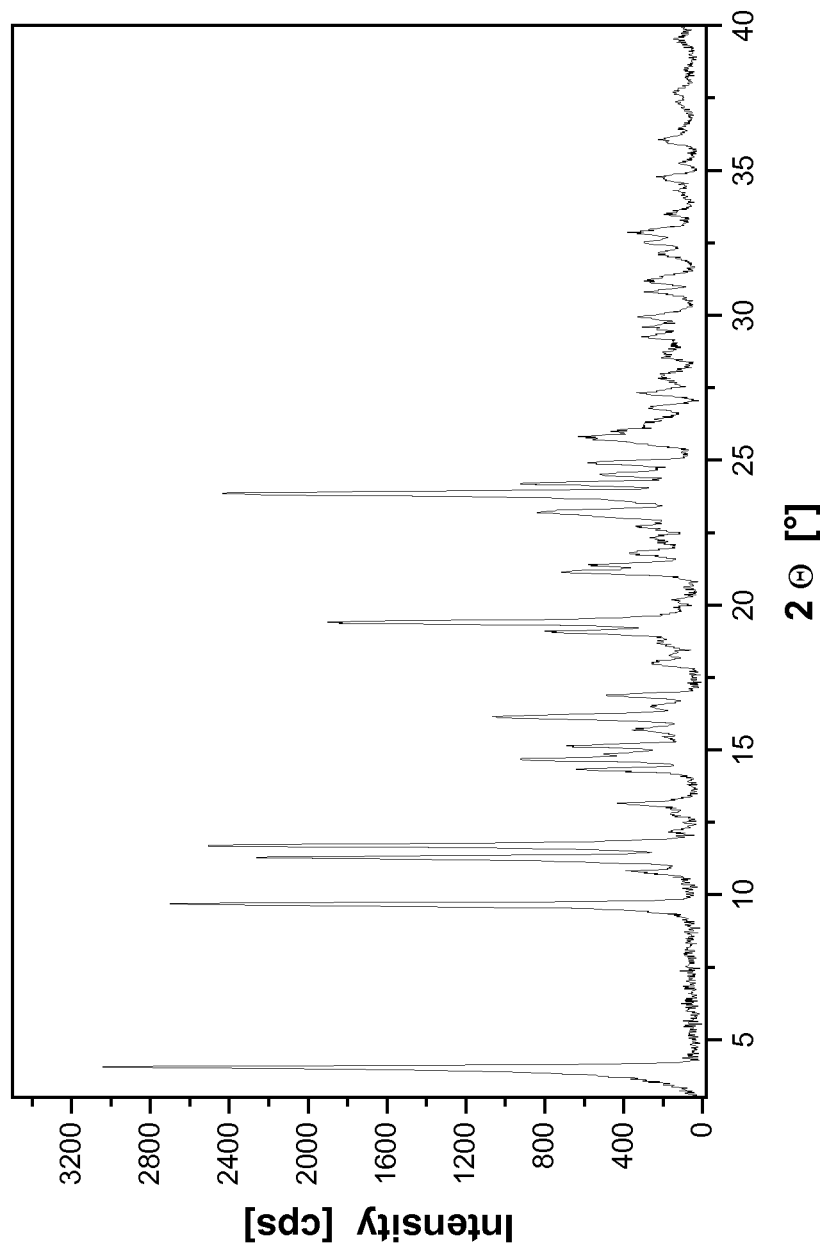

SALT FORMS OF A XANTHINE COMPOUND

The present invention relates to certain salt forms of a xanthine derivative, namely certain salt forms of the pharmaceutically active compound 1-[(4-methyl-quinazolin-2-yl)methyl]-3-methyl-7-(2-butyn-1-yl)-8-(3-(R)-amino-piperidin-1-yl)-xanthine, including amorphous and crystalline forms thereof (including solvate and hydrate forms), and to processes for the manufacture thereof, as well as to the use thereof in pharmaceutical compositions. Methods for treating and/or preventing of diseases which are associated with the enzyme dipeptidyl peptidase IV (DPP-4), such as e.g. metabolic diseases, particularly diabetes (especially type 2 diabetes mellitus) and diseases related thereto, with these compounds as defined herein optionally in combination with one or more other active substances are also contemplated.

In general, salts, solvates, hydrates, polymorphs, crystalline and amorphous forms of a given substance differ often in crystal habits and/or crystalline solid state properties and hence they may have different physical and pharmaceutical properties such as, for example, shape, density, hardness, deformability, stability, purity, hygroscopicity, flowability, compactation, solubility and/or dissolution properties or the like, which may influence, for example, their manufacturability, processability, pharmacokinetic profile (e.g. bioavailability), drug stability (shelf life), administrability and/or formulability or the like, such as e.g. their suitability as solid, semi-solid or liquid pharmaceutical dosage forms, e.g. as tablets, capsules, suspensions, solutions, suppositories or other pharmaceutical dosage forms (including e.g. sustained release formulations or combination preparations comprising a further active ingredient).

A number of xanthine derivatives are already known in the prior art as DPP-4 inhibitors.

The enzyme DPP-4 (dipeptidyl peptidase IV) also known as CD26 is a serine protease known to lead to the cleavage of a dipeptide from the N-terminal end of a number of proteins having at their N-terminal end a prolin or alanin residue. Due to this property DPP-4 inhibitors interfere with the plasma level of bioactive peptides including the peptide GLP-1 and are considered to be promising drugs for the treatment of diabetes mellitus.

For example, DPP-4 inhibitors and their uses, particularly their uses in metabolic (especially diabetic) diseases, are disclosed in WO 2002/068420, WO 2004/018467, WO 2004/018468, WO 2004/018469, WO 2004/041820, WO 2004/046148, WO 2005/051950, WO 2005/082906, WO 2005/063750, WO 2005/085246, WO 2006/027204, WO 2006/029769 or WO2007/014886; or in WO 2004/050658, WO 2004/111051, WO 2005/058901 or WO 2005/097798; or in WO 2006/068163, WO 2007/071738 or WO 2008/017670; or in WO 2007/128721 or WO 2007/128761.

The compound 1-[(4-methyl-quinazolin-2-yl)methyl]-3-methyl-7-(2-butyn-1-yl)-8-(3-(R)-amino-piperidin-1-yl)-xanthine is an orally active DPP-4 inhibitor with therapeutic value for treating type 2 diabetes mellitus, obesity and related diseases.

It has now been found that certain salts of 1-[(4-methyl-quinazolin-2-yl)methyl]-3-methyl-7-(2-butyn-1-yl)-8-(3-(R)-amino-piperidin-1-yl)-xanthine have surprising and useful properties.

Thus, the present invention relates to compounds which are acid addition salts of 1-[(4-methyl-quinazolin-2-yl)methyl]-3-methyl-7-(2-butyn-1-yl)-8-(3-(R)-amino-piperidin-1-yl)-xanthine, especially pharmaceutically acceptable inorganic or organic acid addition salts. Particular mention may be made of the physiologically acceptable salts with inorganic or organic acids customarily used in pharmacy, such as e.g. any of those inorganic and organic acids mentioned below. The salts include water-insoluble and, particularly, water-soluble salts.

BRIEF DESCRIPTION OF THE DRAWINGS

FIG. 9 shows the XRPD diagram of diagram of the tetrahydrate of the hydrochloride salt of BI 1356.

FIG. 10 shows the XRPD diagram of the glycolate salt of BI 1356.

FIG. 11 shows the XRPD diagram of the malonate salt of BI 1356.

FIG. 12 shows the XRPD diagram of the gentisate salt of BI 1356.

DETAILED DESCRIPTION OF THE INVENTION

Figure 1:
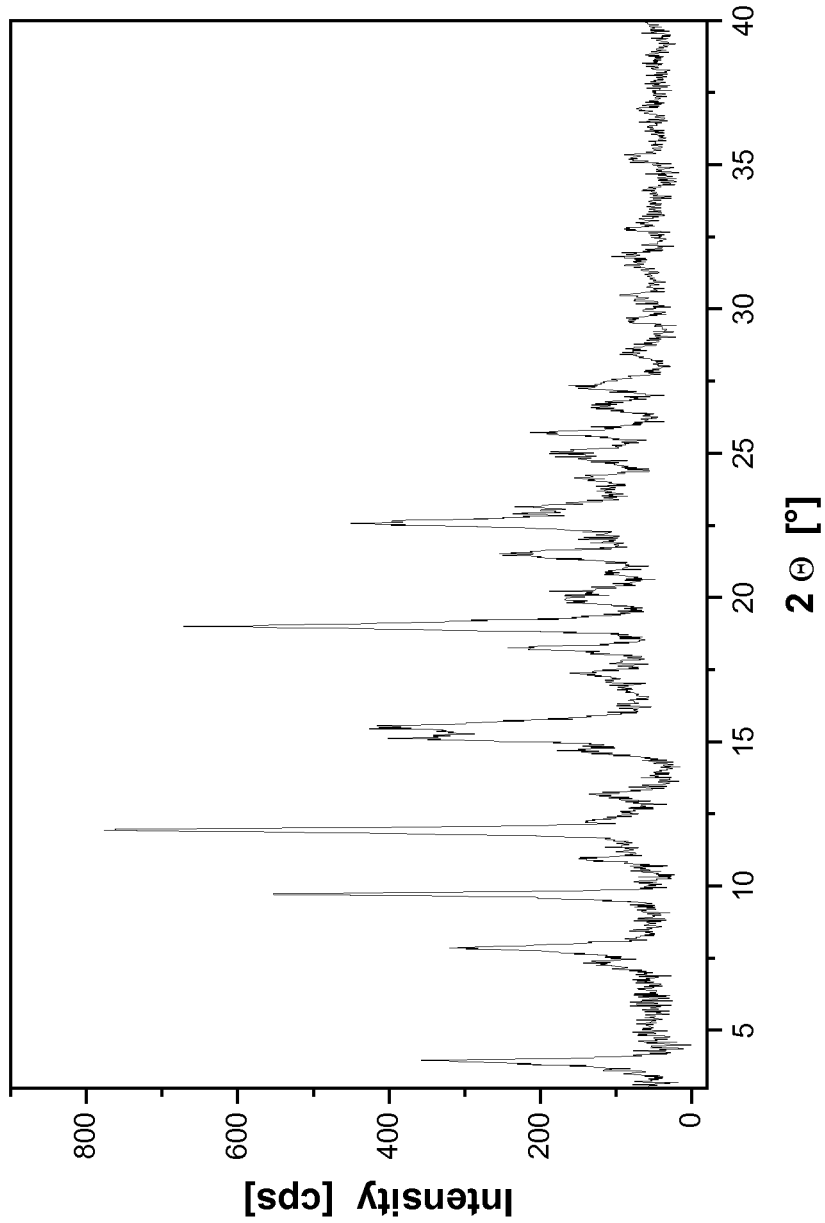
FIG. 1 shows the XRPD diagram of the besylate salt of BI 1356.

Inorganic acids customarily used for forming pharmaceutically acceptable acid addition salts include, by way of example and not limitation, hydrochloric acid, hydrobromic acid, phosphoric acid, nitric acid, sulfuric acid, and the like.

Organic acids customarily used for forming pharmaceutically acceptable acid addition salts include, by way of example and not limitation, acetic acid, 2,2-dichloroacetic acid, adipic acid, ascorbic acid (D- or L-form thereof, especially the L-form thereof), aspartic acid (D- or L-form thereof, especially the L-form thereof), benzenesulfonic acid, benzoic acid, 4-acetamido-benzoic acid, camphoric acid ((+)- or (−)-form thereof, especially the (+)-form thereof), camphor-10-sulfonic acid ((+)- or (−)-form thereof, especially the (+)-form thereof), capric acid (decanoic acid), caproic acid (hexanoic acid), caprylic acid (octanoic acid), carbonic acid, cinnamic acid, citric acid, cyclamic acid, dodecylsulfuric acid, ethane-1,2-disulfonic acid, ethanesulfonic acid, 2-hydroxy-ethanesulfonic acid, formic acid, fumaric acid, galactaric acid, gentisic acid, glucoheptonic acid (D- or L-form thereof, especially the D-form thereof), gluconic acid (D- or L-form thereof, especially the D-form thereof); glucuronic acid (D- or L-form thereof, especially the D-form thereof), glutamic acid, glutaric acid, 2-oxo-glutaric acid, glycerophosphoric acid, glycolic acid, hippuric acid, isobutyric acid, lactic acid (D- or L-form thereof), lactobionic acid, lauric acid, maleic acid, malic acid (D- or L-form thereof), malonic acid, mandelic acid (D- or L-form thereof), methanesulfonic acid, naphthalene-1,5-disulfonic acid, naphthalene-2-sulfonic acid, 1-hydroxy-2-naphthoic acid, nicotinic acid, oleic acid, orotic acid, oxalic acid, palmitic acid, pamoic acid (embonic acid), propionic acid, pyroglutamic acid (D- or L-form thereof, especially the L-form thereof), salicyclic acid, 4-aminosalicyclic acid, sebacic acid, stearic acid, succinic acid, tartaric acid (D- or L-form thereof), thiocyanic acid, toluenesulfonic acid (especially the p-isomer thereof), undecylenic acid, and the like.

A class of above-mentioned organic acids includes carboxylic acid derivatives. Another class of above-mentioned organic acids includes sulfonic acid derivatives.

The acids may be monobasic or polybasic acids, illustrative polybasic acids are dibasic or tribasic. These polybasic acids can be, depending on their nature, substantially singly, twicely or tricely deprotonated, typically they are substantially singly deprotonated.

For example, in carboxylic acid salts the acid can be a mono- or polycarboxylic acid having one or, respectively, two or more carboxylic acid groups. In a first sub-class of polycarboxylic acid salts, the polycarboxylic acids in these salts can be substantially singly deprotonated, as for example in the case of a dicarboxylic acid salt having a 1:1 stoichiometry of free compound and dicarboxylic acid. In a second sub-class of polycarboxylic acid salts, the polybasic carboxylic acid and the free compound can be in a substantially 1:1 stoichiometry, irrespective of the number of carboxylic acid groups in the acid.

A sub-group of above-mentioned inorganic or organic acids includes, by way of example and not limitation, acetic, adipic, L-ascorbic, capric, carbonic, citric, fumaric, galactaric, D-glucoheptanoic, D-gluconic, D-glucuronic, glutamic, glutaric, glycerophosphoric, hippuric, hydrochloric, D- or L-lactic, lauric, maleic, (−)-L-malic, phosphoric, sebacic, succinic, sulphuric, (+)-L-tartaric and thiocyanic acid.

Another sub-group of above-mentioned inorganic or organic acids includes, by way of example and not limitation, alginic, benzenesulfonic, benzoic, (+)-camphoric, caprylic, cyclamic, dodecylsulfuric, ethane-1,2-disulfonic, ethanesulfonic, 2-hydroxy-ethanesulfonic, gentisic, 2-oxoglutaric, isobutyric, lactobionic, malonic, methanesulfonic, naphthalene-1,5-disulfonic, naphthalene-2-sulfonic, 1-hydroxy-2-naphthoic, nicotinic, oleic, orotic, oxalic, pamoic, propionic, (−)-L-pyroglutamic and p-toluenesulfonic acid.

The acids are employed in salt preparation—depending on whether a mono- or polybasic acid is concerned and depending on which salt is desired—in an equimolar quantitative ratio or one differing therefrom.

Thus, within the acid addition salts of this invention the acid and the free compound may be substantially in 1:1 stoichiometry or one differing therefrom, such as e.g. from about 1:2 to about 2:1 stoichiometry. Non-integral stoichiometry ratios may be also possible, such as e.g. 1:1.5 or 1.5:1.

A certain sub-group of acid addition salts with inorganic or organic acids includes, by way of example and not limitation, the hydrochloride, mesylate, hydrobromide, acetate, fumarate, sulfate, succinate, citrate, phosphate, maleate, tartrate, lactate, benzoate and carbonate salt.

Another certain sub-group of acid addition salts with inorganic or organic acids includes, by way of example and not limitation, the hydrochloride, sulphate, tartrate, maleate, citrate, phosphate, acetate, lactate and fumarate salt.

The invention also includes mixtures of salts.

Furthermore, any salt given herein is intended to embrace all tautomers, hydrates, solvates, crystalline, amorphous and polymorphous forms thereof, as well as mixtures thereof.

Those skilled in the art will appreciate that organic compounds can be isolated in association with solvent molecules or can form complexes with solvents in which they are reacted or from which they are precipitated, crystallized or isolated. According to expert's awareness, some of the salts according to this invention may contain, e.g. when isolated in solid form, varying or fixed amounts of solvents (including aqueous and/or non-aqueous solvents). Included within the scope of the invention are therefore solvates (including hydrates, organic solvates and mixed hydrates/organic solvates) of the salts according to this invention. Solvates of the salt forms according to this invention include stoichiometric and non-stoichiometric solvates. Preferably the solvent(s) used is a pharmaceutically acceptable solvent(s), e.g. water and/or ethanol or the like. The present invention embraces both the unsolvated and all solvated forms. Likewise, the present invention embraces all hydrate, anhydrous, hygroscopic and/or non-hygroscopic forms.

In a further aspect, the present invention relates to compounds which are solvates of the salts according to this invention either in simple, such as e.g. solvates comprising an organic solvent alone or water alone, or in mixed form, such as e.g. mixed solvates comprising at least one organic solvent, such as e.g. a low molecular weight aliphatic alcohol, with water (e.g. mixed hydrates/solvates), or mixed solvates comprising at least two different organic solvents with or without water, in any mixing ratios, including homosolvates (solvates in which there is solely one type of solvent) and heterosolvates (solvates in which there are two or more different types of solvents).

For more detailed example, solvates of the salts according to this invention include hydrates and alcoholates (solvates with alcohol, such as e.g. ethanol) as well as mixtures thereof (including mixed hydrates/alcoholates).

The one or more solvents may be present in an non-stoichiometric amount or in a stoichiometric amount, such as e.g. 0.5:1, 1:1, 1.5:1, 2:1, 3:1, or 4:1 molar ratio based on the amount of the solvate-free salt. Where the crystalline forms are solvated, they may contain, for example, up to four molecules of solvens, more usually up to two or three molecules, e.g. one molecule of solvent or two molecules of solvents. Non-stoichiometric solvates may also be formed in which the number of molecules of solvent present is less than one or is otherwise a non-integer, such as e.g., where there is less than one molecule of solvent present, there may be for example 0.4, or 0.5, or 0.6, or 0.7, or 0.8, or 0.9 molecules of solvent present per molecule of compound. For example, solvates or hydrates of the salts according to this invention include, without being limited to, hemi-, mono-, sesqui-, di-, tri- and tetrasolvates or -hydrates, respectively. Stoichiometric and non-stoichiometric mixed solvates of these hydrates with one or more organic solvents (such as e.g. with an alcohol, particularly ethanole) in any mixing ratios are also contemplated within this invention.

In a certain embodiment, the present invention relates to hydrates, solvates with ethanol (ethanolates) and mixed hydrates/ethanolates of the salts of this invention.

Within the solvates of this invention, the solvent molecules can be incorporated into the solid-state structure (such as e.g. they may be become trapped in the crystals upon isolation) or not (such as e.g. they may be retained on the surface of the crystals). When the solvent or water is tightly bound (as e.g. in isolated site solvates), the complex has often a well defined stoichiometry independent of humidity. When, however, the solvent or water is weakly bound (as e.g. in channel solvates and in hygroscopic compounds), the water/solvent content is often dependent on humidity and/or drying conditions and the non-stoichiometry is the norm.

Pharmaceutically non-acceptable salts (including their solvates and hydrates), which can be obtained, for example, as process products during the manufacture on an industrial scale, can be converted into pharmaceutically acceptable salts (including their solvates and hydrates) by processes known to the person skilled in the art, e.g. by salt and/or solvate exchange or displacement, or via the salt- and/or solvate-free compound (with or without isolation).

Salts (including solvates, hydrates and/or other forms) which are unsuitable for pharmaceutical uses but which can be employed, for example, for the isolation or purification of the free compound 1-[(4-methyl-quinazolin-2-yl)methyl]-3-methyl-7-(2-butyn-1-yl)-8-(3-(R)-amino-piperidin-1-yl)-xanthine or of their pharmaceutically acceptable salts (including solvates, hydrates and/or other forms), are also included within this invention.

A particular embodiment of this invention relates to an acid addition salt of 1-[(4-methyl-quinazolin-2-yl)methyl]-3-methyl-7-(2-butyn-1-yl)-8-(3-(R)-amino-piperidin-1-yl)-xanthine selected from the group consisting of a besylate salt, a hydrobromide salt, a benzoate salt, an esylate salt, a fumarate salt, a mesylate salt, a salicylate salt, a tosylate salt, a hydrochloride salt, a glycolate salt, a malonate salt and a gentisate salt, as well as the solvates, in particular the organic solvates, the hydrates and the mixed organic solvates/hydrates thereof.

The salts (including their solvate, hydrate and/or other forms) of this invention can be obtained by methods known to the skilled person for making acid addition salts, e.g. these salts can be prepared (e.g. in situ) during the final reaction, deprotection, isolation, purification and/or further processing of the free compound (or prodrug, precursor or protected compound), or by reacting the free compound with the desired acid or a suitable anion exchange reagent, such as e.g. via a process comprising one or more of the steps described herein. Typically, the free compound is combined with the desired acid, e.g. by dissolving, dispersing or slurrying the free compound in a suitable solvent or mixture of solvents, which contains the desired acid, or to which the desired acid (optionally dissolved in a suitable solvent or mixture of solvents) is then added, or vice versa, with or without heating (e.g. dissolving, mixing and/or reacting can be conducted at ambient temperature or at elevated temperature (such as e.g. from about 30° C. to 70° C. or from 40° C. to 60° C.) or at the boiling temperature of the solvent(s) used, such as temperatures up to 100° C. may be applied to form solutions). The salts can be isolated, e.g. by filtering, crystallization, precipitating e.g. with a nonsolvent for the addition salt or by cooling, or by concentrating (e.g. by heating, removing or evaporating the solvent), and, if desired, purified, e.g. by re-crystallization from an appropriate re-crystallization solvent or mixture of solvents by methods customary to one of skill in the art (e.g. analogously or similarly as described afore), and/or, if required, the process further comprises, at a suitable stage, removing or separating any undesired material or impurities, and finally, optionally, the salts may be washed and/or dried.

In general, solvents, which the skilled person may consider within this invention, may include, without being limited to, organic, non-aqueous or aqueous, protic or aprotic, polar or apolar solvents, such as, for example, ketones such as e.g. acetone, methyl ethyl ketone, methyl propyl ketone, methyl tert- or isobutyl ketone or the like, lactones such as e.g. valerolactone, ethers such as e.g. diethyl ether, diisopropyl ether, ethylene glycol dimethyl ether, tetrahydrofuran, dioxane or the like, hydrocarbons such as e.g. toluene, hexane or the like, chlorinated hydrocarbons such as e.g. methylene chloride, chloroform or the like, low-molecular-weight aliphatic alcohols such as e.g. methanol, ethanol, 1-propanol, isopropanol, butanol or the like, esters such as e.g. acetic acid lower alkyl esters (e.g. ethyl acetate) or the like, amides or lactames such as e.g. N,N-dimethylformamide, N-methyl-2-pyrrolidone or the like, nitriles such as e.g. acetonitrile or the like, or sulfoxides such as e.g. DMSO or the like, or water, or mixtures thereof.

Appropriate solvents or nonsolvents may be determined by solubility tests in various solvents.

Within the meaning of this invention, as particular solvents may be mentioned organic solvents which are wholly or partly water miscible, such as e.g. a suitable solvent for salt formation and/or crystallization is a low-molecular-weight aliphatic alcohol, e.g. ethanol, optionally in combination with water.

In a further aspect, the present invention relates to a process for preparing a salt of the invention, particularly in crystalline form, which comprises one or more of the steps of:
i.) forming a solution comprising 1-[(4-methyl-quinazolin-2-yl)methyl]-3-methyl-7-(2-butyn-1-yl)-8-(3-(R)-amino-piperidin-1-yl)-xanthine and an acid, such as e.g. any of those pharmaceutically acceptable acids described herein, particularly any of those described by way of example in the following examples,
ii.) inducing crystallization of the salt e.g. from solution, and
iii.) recovering the crystalline 1-[(4-methyl-quinazolin-2-yl)methyl]-3-methyl-7-(2-butyn-1-yl)-8-(3-(R)-amino-piperidin-1-yl)-xanthine salt.

In embodiments of this method, 1-[(4-methyl-quinazolin-2-yl)methyl]-3-methyl-7-(2-butyn-1-yl)-8-(3-(R)-amino-piperidin-1-yl)-xanthine and the acid are in 1:1 stoichiometry.

In further embodiments of this method, reacting and/or (re-)crystallization may be performed in an alcohol (particularly ethanol), optionally in the presence of water.

Salts prepared can be converted to another, e.g. by reaction with an appropriate acid or by means of a suitable ion exchanger. Likewise, salts obtained can be converted into the free compounds (e.g. via neutralization with a suitable base, with or without isolation of the free base, e.g. by extraction), which can in turn be converted into salts, by acidification. In this manner, physiologically unacceptable salts can be converted into physiologically acceptable salts.

In a further aspect, the present invention relates to salts of the invention (including their solvates and hydrates) in solid forms, including amorphous, semi-amorphous, polymorphous, semi-crystalline and crystalline forms, as well as mixtures thereof.

For more detailed example, the invention concerns the salts (including their solvates and hydrates whether mixed or not) of the invention in partially crystalline form (such as e.g. from about 5 to 20% crystalline) as well as in substantially crystalline form (such as e.g. greater than any of about 20, 30, 40, 50, 60, 70, 80, 90 or 95% crystalline).

The presence of crystal forms and degree (%) of crystallinity may be determined by the skilled person using X-ray powder diffraction (XRPD). Other techniques, such as solid state NMR, FT-IR, Raman spectroscopy, differential scanning calorimetry (DSC) and microcalorimetry, may also be used.

The crystalline forms and polymorphs of the salts of the present invention may be characterized by their melting points (obtained e.g. by DSC method) or by their respective x-ray powder diffraction spectra data or pattern comprising major peaks (e.g. with a relative intensity of greater than or equal about 10%, 20% or 25% or the like), as shown in the examples hereinafter. Such as for example, a crystalline form of the hydrochloride salt of this invention has the X-ray powder diffraction pattern essentially as defined in Table 10 and/or essentially as defined in FIG. 9.

Crystalline forms and polymorphs may be prepared by crystallization of a compound of this invention. Various crystallization techniques may be used to form and isolate crystalline compounds and polymorphs, such as e.g. any of those crystalline forming procedures described herein, such as, for example, crystallization or precipitation from a suitable solvent or solvent mixtures, stirring of a suspension (phase equilibration), slurrying, solvent evaporation, allowing or causing cooling to a suitable temperature to initiate crystallization, using suitable modes of cooling ranging from very fast to very slow cooling rates during crystallization, effecting a suitable pressure, using seeding crystals, re-crystallization, filtering, washing (e.g. in the crystallising solvent) and/or drying (e.g. under reduced pressure and/or at elevated temperature).

Crystalline forms may also be obtained by heating or melting a form obtained followed by gradual or fast cooling; in this manner one polymorph or one crystalline form may be converted to another.

In a further aspect, the present invention relates to salts of the invention (including their solvates, hydrates, polymorphs, crystalline and amorphous forms) in substantially pure form (e.g. substantially devoid of impurities and/or other forms), for example, in a degree of purity of about >80%, >85%, >90%, >95%, >98%, or >99% of the respective form.

In another aspect, the present invention relates to salts of the invention (including their solvates, hydrates, polymorphs, crystalline and amorphous forms) in substantially pure form, that means, for example, that the respective form includes less than 20%, less than 10%, less than 5%, less than 3% or less than 1% by weight of any impurities or other physical forms.

The present invention further relates to a salt as described herein for use in the treatment and/or prevention of metabolic diseases, particularly type 2 diabetes mellitus.

The present invention further relates to the use of a salt as described herein for the manufacture of a pharmaceutical composition for treating and/or preventing metabolic diseases, particularly type 2 diabetes mellitus.

The present invention further relates to a pharmaceutical composition for use in the treatment and/or prevention of metabolic diseases, particularly type 2 diabetes mellitus, said pharmaceutical composition comprising a salt as described herein and optionally one or more pharmaceutically acceptable carriers and/or diluents.

The present invention further relates to a fixed or non-fixed combination including a kit-of-parts for use in the treatment and/or prevention of metabolic diseases, particularly type 2 diabetes mellitus, said combination comprising a salt as described herein and optionally one or more other active substances, e.g. any of those mentioned herein.

The present invention further relates to the use of a salt as described herein in combination with one or more other active substances, such as e.g. any of those mentioned herein, for the manufacture of a pharmaceutical composition for treatment and/or prevention of metabolic diseases, particularly type 2 diabetes mellitus.

The present invention further relates to a pharmaceutical composition for use in the treatment and/or prevention of metabolic diseases, particularly type 2 diabetes mellitus, said pharmaceutical composition comprising a salt as described herein and optionally one or more other active substances, such as e.g. any of those mentioned herein.

The present invention further relates to a method of treating and/or preventing metabolic diseases, particularly type 2 diabetes mellitus, said method comprising administering to a subject in need thereof (particularly a human patient) an effective amount of a salt as described herein, optionally separately, sequentially, simultaneously, concurrently or chronologically staggered with an effective amount of one or more other active substances, such as e.g. any of those mentioned herein.

Further, the salts as described herein may be useful in one or more of the following methods
for preventing, slowing progression of, delaying, or treating a metabolic disorder;
for improving glycemic control and/or for reducing of fasting plasma glucose, of postprandial plasma glucose and/or of glycosylated hemoglobin HbA1c;
for preventing, slowing, delaying or reversing progression from impaired glucose tolerance, insulin resistance and/or from metabolic syndrome to type 2 diabetes mellitus;
for preventing, slowing progression of, delaying or treating of a condition or disorder selected from the group consisting of complications of diabetes mellitus;
for reducing the weight or preventing an increase of the weight or facilitating a reduction of the weight;
for preventing or treating the degeneration of pancreatic beta cells and/or for improving and/or restoring the functionality of pancreatic beta cells and/or stimulating and/or restoring the functionality of pancreatic insulin secretion; and/or
for maintaining and/or improving the insulin sensitivity and/or for treating or preventing hyperinsulinemia and/or insulin resistance.

Examples of such metabolic diseases or disorders amenable by the therapy of this invention may include, without being restricted to, Type 1 diabetes, Type 2 diabetes, inadequate glucose tolerance, insulin resistance, hyperglycemia, hyperlipidemia, hypercholesterolemia, dyslipidemia, metabolic syndrome X, obesity, hypertension, chronic systemic inflammation, retinopathy, neuropathy, nephropathy, atherosclerosis, endothelial dysfunction and osteoporosis.

The compound 1-[(4-methyl-quinazolin-2-yl)methyl]-3-methyl-7-(2-butyn-1-yl)-8-(3-(R)-amino-piperidin-1-yl)-xanthine (compare WO 2004/018468, example 2 (142)), which is also known as BI 1356, has the formula:

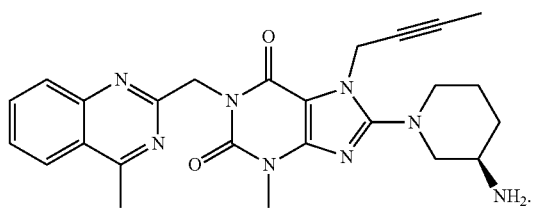 [SMILES: CC#CCn1c(N2CCC[C@@H](N)C2)nc2c1c(=O)n(Cc1nc(C)c3ccccc3n1)c(=O)n2C]

The methods of synthesis for 1-[(4-methyl-quinazolin-2-yl)methyl]-3-methyl-7-(2-butyn-1-yl)-8-(3-(R)-amino-piperidin-1-yl)-xanthine are known to the skilled person. Advantageously, 1-[(4-methyl-quinazolin-2-yl)methyl]-3-methyl-7-(2-butyn-1-yl)-8-(3-(R)-amino-piperidin-1-yl)-xanthine can be prepared using synthetic methods as described in the literature. Thus, for example, it can be obtained as described in WO 2002/068420, WO 2004/018468 or WO 2006/048427, the disclosures of which are incorporated herein.

For pharmaceutical application in warm-blooded vertebrates, particularly humans, usually dosage levels from 0.001 to 100 mg/kg body weight, preferably at 0.1-15 mg/kg, in each case 1 to 4 times a day, of active ingredient may be used. For this purpose, the compounds, optionally combined with other active substances, may be incorporated together with one or more inert conventional carriers and/or diluents, e.g. with corn starch, lactose, glucose, microcrystalline cellulose, magnesium stearate, polyvinylpyrrolidone, citric acid, tartaric acid, water, water/ethanol, water/glycerol, water/sorbitol, water/polyethylene glycol, propylene glycol, cetylstearyl alcohol, carboxymethylcellulose or fatty substances such as hard fat or suitable mixtures thereof into conventional galenic preparations such as plain or coated tablets, capsules, powders, suspensions or suppositories.

Usual liquid or solid carrier materials are not only inorganic, but also organic carrier materials. Thus, for example, lactose, corn starch or derivatives thereof, talc, stearic acid or its salts may be used as carrier materials for tablets, coated tablets, dragees and hard gelatine capsules. Typical carrier materials for soft gelatine capsules are, for example, vegetable oils, waxes, fats and semi-solid and liquid polyols (depending on the nature of the active ingredient no carriers are, however, required in the case of soft gelatine capsules). Typical carrier materials for the production of solutions and syrups are, for example, water, polyols, sucrose, invert sugar and the like. Typical carrier materials for injection solutions are, for example, water, alcohols, polyols, glycerol and vegetable oils. Typical carrier materials for suppositories are, for example, natural or hardened oils, waxes, fats and semi-liquid or liquid polyols.

The pharmaceutical compositions according to this invention comprising the salts as defined herein are thus prepared by the skilled person using pharmaceutically acceptable formulation excipients as described in the art, such as e.g. those mentioned hereinabove and hereinbelow, of a type appropriate, e.g. to the desired formulation and to the desired mode of administration. The content of the active compound(s) is advantageously being from 0.1 to 95 wt % (weight percent of the final dosage form), particularly from 1 to 60 wt %. By means of the appropriate selection of the excipients, it is possible to obtain a pharmaceutical administration form adapted to the active ingredient(s) and/or to the desired onset and/or duration of action. Examples of such excipients include, without being restricted to, excipients commonly used for solid pharmaceutical forms (e.g. tablets), such as e.g. diluents, fillers, binders, carriers, lubricants, disintegrants, flow promoters, glidants and/or coating agents, excipients commonly used for liquid oral forms (e.g. syrups or elixirs), such as e.g. gel formers, wetting agents, antifoams, colorants, adsorbent agents, thickeners, flavorings and/or sweeteners, excipients commonly used for injection solutions or infusions, such as e.g. dispersants, emulsifiers, preservatives, solubilizers, buffer substances and/or isotonic adjusting substances, and other accessory excipients, such as e.g. stabilizers and/or solvents.

An embodiment of this invention refers to dosage forms for oral administration of the compounds of the invention. Tablets, coated tablets, dragees, pills, cachets, capsules, caplets, granules, solutions, emulsions and suspensions are e.g. suitable for oral administration. Solid oral dosage forms, such as e.g. capsules, tablets, pills, powders or granules, are hereby particularly concerned.

If desired, these formulations may also be adapted so as to represent, for example, an enteric form, an immediate release form, a delayed release form, a repeated dose release form, a prolonged release form or a sustained release form. Said forms can be obtained, for example, by coating tablets, by matrix techniques, by dividing tablets (e.g. their cores and/or coatings) into several compartments which may be separated by layers disintegrating under different conditions (e.g. pH conditions) or by coupling the compound of the invention to a biodegradable polymer.

In a certain embodiment, a compound of the invention is preferably in the form of a tablet. Such a tablet typically comprises the active ingredient(s) with one or more diluents, fillers and/or carriers, and, optionally, one or more binders, one or more lubricants, one or more disintegrants, and/or one or more glidants, as well as, if desired, a film overcoat.

Such a tablet may be obtained, for example, by mixing the active substance(s) with known excipients, for example which can be selected from those mentioned herein.

Coated tablets may be prepared by coating of cores (which may be produced analogously to the tablets) with substances normally used for tablet coatings (e.g. film-forming agents, plasticizers, glidants and/or pigments).

The tablet (including its core and coating) may also comprise several layers (e.g. mono-, bi- or trilayer), e.g. to achieve delayed release or to prevent incompatibilities.

Usually, in general as diluents/fillers one or more of mannitol, lactose, sucrose, maltodextrin, sorbitol, xylitol, powdered cellulose, microcrystalline cellulose, carboxymethylcellulose, carboxyethylcellulose, methylcellulose, ethylcellulose, hydroxyethylcellulose, hydroxypropylcellulose, methylhydroxyethylcellulose, starch, sodium starch glycolate, pregelatinized starch, a calcium phosphate, a metal carbonate, a metal oxide or a metal aluminosilicate may come into consideration.

Usually, in general as binders one or more of polyvinylpyrrolidone, copovidone, hydroxypropylcellulose, hydroxypropylmethylcellulose, crosslinked poly(acrylic acid), gum arabic, gum acacia, gum tragacanath, lecithin, casein, polyvinyl alcohol, gelatin, kaolin, cellulose, methylcellulose, hydroxymethylcellulose, carboxymethylcellulose, carboxymethylcellulose calcium, carboxymethylcellulose sodium, hydroxypropylcellulose, hydroxypropylmethylcellulose phthalate, hydroxyethylcellulose, methylhydroxyethylcellulose, silicified microcrystalline cellulose, starch, maltodextrin, dextrins, microcrystalline cellulose or sorbitol may come into consideration.

Usually, in general as disintegrants one or more of croscarmellose sodium, carmellose calcium, crospovidone, alginic acid, sodium alginate, potassium alginate, calcium alginate, an ion exchange resin, an effervescent system based on food acids and an alkaline carbonate component, clay, talc, starch, pregelatinized starch, sodium starch glycolate, cellulose floc, carboxymethylcellulose, hydroxypropylcellulose, calcium silicate, a metal carbonate, sodium bicarbonate, calcium citrate or calcium phosphate may come into consideration.

Usually, in general as lubricants one or more of stearic acid, metallic stearate, sodium stearyl fumarate, fatty acid, fatty alcohol, fatty acid ester, glyceryl behenate, mineral oil, vegetable oil, paraffin, leucine, silica, silicic acid, talc, propylene glycol fatty acid ester, polyethylene glycol, polypropylene glycol, polyalkylene glycol or sodium chloride may come into consideration.

If desired, direct compression or granulation of the mixtures and/or components may be considered, which may be accomplished by conventional granulation techniques known to one of skill in the art. For example, dry granulation techniques include, but are not limited to, compression of the mixed powder under high pressure, either by roller compaction or "slugging" in a heavy-duty tablet press. Wet granulation techniques include, but are not limited to, high shear granulation, single-pot processing, top-spray granulation, bottom-spray granulation, fluidized spray granulation, extrusion/spheronization, and rotor granulation.

Examples of suitable diluents for compounds of this invention may include cellulose powder, calcium hydrogen phosphate, erythritol, low substituted hydroxypropyl cellulose, mannitol, pregelatinized starch or xylitol.

Examples of suitable lubricants for compounds of this invention may include talc, polyethyleneglycol, calcium behenate, calcium stearate, hydrogenated castor oil or magnesium stearate.

Examples of suitable binders for compounds of this invention may include copovidone (copolymerisates of vinylpyrrolidon with other vinylderivates), hydroxypropyl methylcellulose (HPMC), hydroxypropylcellulose (HPC), polyvinylpyrrolidon (povidone), pregelatinized starch, or low-substituted hydroxypropylcellulose (L-HPC).

Examples of suitable disintegrants for compounds of this invention may include corn starch or crospovidone.

Suitable methods of preparing pharmaceutical formulations of the compounds of this invention may be
- direct tabletting of the active substance in powder mixtures with suitable tabletting excipients;
- granulation with suitable excipients and subsequent mixing with suitable excipients and subsequent tabletting as well as film coating; or
- packing of powder mixtures or granules into capsules.

Suitable granulation methods may be
- wet granulation in the intensive mixer followed by fluidised bed drying;
- one-pot granulation;
- fluidised bed granulation; or
- dry granulation (e.g. by roller compaction) with suitable excipients and subsequent tabletting or packing into capsules.

Particular formulations and their preparation are described in the patent application WO 2007/128724, the contents of which are incorporated herein in their entirety for all purposes.

Within the present invention, the dosage typically required when administered intravenously is 0.1 mg to 10 mg, preferably 0.25 mg to 5 mg, and when administered orally is 0.5 mg to 100 mg, preferably 2.5 mg to 50 mg or 0.5 mg to 10 mg, more preferably 2.5 mg to 10 mg or 1 mg to 5 mg, in each case 1 to 4 times a day, of active ingredient. Thus, e.g. the dosage of 1-[(4-methyl-quinazolin-2-yl)methyl]-3-methyl-7-(2-butyn-1-yl)-8-(3-(R)-amino-piperidin-1-yl)-xanthine when administered orally is 0.5 mg to 10 mg per patient per day, preferably 2.5 mg to 10 mg or 1 mg to 5 mg per patient per day.

A dosage form prepared with a pharmaceutical composition comprising a salt as mentioned herein contain the active ingredient in a dosage range of 0.1-100 mg. Thus, e.g. particular dosage strengths of 1-[(4-methyl-quinazolin-2-yl)methyl]-3-methyl-7-(2-butyn-1-yl)-8-(3-(R)-amino-piperidin-1-yl)-xanthine are 0.5 mg, 1 mg, 2.5 mg, 5 mg and 10 mg.

A special embodiment of this invention refers to those orally administered DPP-4 inhibitors which are therapeutically efficacious at low dose levels, e.g. at dose levels <100 mg or <70 mg per patient per day, preferably <50 mg, more preferably <30 mg or <20 mg, even more preferably from 1 mg to 10 mg, particularly from 1 mg to 5 mg (more particularly 5 mg) of active ingredient, per patient per day, preferentially, administered orally once-daily, more preferentially, at any time of day, administered with or without food.

For details on dosage forms, formulations and administration of active substances, particularly of those indicated herein, reference is made to respective scientific literature and/or published patent documents, particularly to those cited herein.

As different metabolic functional disorders often occur simultaneously, it is quite often indicated to combine a number of different active principles with one another. Thus, depending on the functional disorders diagnosed, improved treatment outcomes may be obtained if a DPP-4 inhibitor is combined with active substances customary for the respective disorders, such as e.g. one or more active substances selected from among the other antidiabetic substances, especially active substances that lower the blood sugar level or the lipid level in the blood, raise the HDL level in the blood, lower blood pressure or are indicated in the treatment of atherosclerosis or obesity.

The compounds of this invention—besides their use in mono-therapy—may also be used in conjunction with other active substances, by means of which improved treatment results can be obtained. Such a combined treatment may be given as a free combination of the substances or in the form of a fixed combination, for example in a tablet or capsule. Pharmaceutical formulations of the combination partner needed for this may either be obtained commercially as pharmaceutical compositions or may be formulated by the skilled man using conventional methods. The active substances which may be obtained commercially as pharmaceutical compositions are described in numerous places in the prior art, for example in the list of drugs that appears annually, the "Rote Liste®" of the federal association of the pharmaceutical industry, or in the annually updated compilation of manufacturers' information on prescription drugs known as the "Physicians' Desk Reference".

Examples of antidiabetic combination partners are metformin; sulphonylureas such as glibenclamide, tolbutamide, glimepiride, glipizide, gliquidon, glibornuride and gliclazide; nateglinide; repaglinide; thiazolidinediones such as rosiglitazone and pioglitazone; PPAR gamma modulators such as metaglidases; PPAR-gamma agonists such as GI 262570; PPAR-gamma antagonists; PPAR-gamma/alpha modulators such as tesaglitazar, muraglitazar and KRP297; PPAR-gamma/alpha/delta modulators; AMPK-activators such as AICAR; acetyl-CoA carboxylase (ACC1 and ACC2) inhibitors; diacylglycerol-acetyltransferase (DGAT) inhibitors; pancreatic beta cell GCRP agonists such as SMT3-receptor-agonists and GPR119; 11β-HSD-inhibitors; FGF19 agonists or analogues; alpha-glucosidase blockers such as acarbose, voglibose and miglitol; alpha2-antagonists; insulin and insulin analogues such as human insulin, insulin lispro, insulin glusilin, r-DNA-insulinaspart, NPH insulin, insulin detemir, insulin zinc suspension and insulin glargin; Gastric inhibitory Peptide (GIP); pramlintide; amylin or GLP-1 and GLP-1 analogues such as Exendin-4; SGLT2-inhibitors such as KGT-1251; inhibitors of protein tyrosine-phosphatase; inhibitors of glucose-6-phosphatase; fructose-1,6-bisphosphatase modulators; glycogen phosphorylase modulators; glucagon receptor antagonists; phosphoenolpyruvatecarboxykinase (PEPCK) inhibitors; pyruvate dehydrogenasekinase (PDK) inhibitors; inhibitors of tyrosine-kinases (50 mg to 600 mg) such as PDGF-receptor-kinase (cf. EP-A-564409, WO 98/35958, U.S. Pat. No. 5,093,330, WO 2004/005281, and WO 2006/041976); glucokinase/regulatory protein modulators incl. glucokinase activators; glycogen synthase kinase inhibitors; inhibitors of the SH2-domain-containing inositol 5-phosphatase type 2 (SHIP2); IKK inhibitors such as high-dose salicylate; JNK1 inhibitors; protein kinase C-theta inhibitors; beta 3 agonists such as ritobegron, YM 178, solabegron, talibegron, N-5984, GRC-1087, rafabegron, FMP825; aldosereductase inhibitors such as AS 3201, zenarestat, fidarestat, epalrestat, ranirestat, NZ-314, CP-744809, and CT-112; SGLT-1 or SGLT-2 inhibitors; KV 1.3 channel inhibitors; GPR40 modulators; SCD-1 inhibitors; CCR-2 antagonists; and other DPP IV inhibitors.

Metformin is usually given in doses varying from about 500 mg to 2000 mg up to 2500 mg per day using various dosing regimens from about 100 mg to 500 mg or 200 mg to 850 mg (1-3 times a day), or about 300 mg to 1000 mg once or twice a day, or delayed-release metformin in doses of about 100 mg to 1000 mg or preferably 500 mg to 1000 mg once or twice a day or about 500 mg to 2000 mg once a day. Particular dosage strengths may be 250, 500, 625, 750, 850 and 1000 mg of metformin hydrochloride.

A dosage of pioglitazone is usually of about 1-10 mg, 15 mg, 30 mg, or 45 mg once a day, e.g. used as pioglitazone hydrochloride.

Glibenclamide (glyburide) is usually given in doses from 2.5 to 20 mg once (or twice) a day (typical dosage strengths are 1.25, 2.5 and 5 mg), or micronized glibenclamide in doses from 0.75 to 12 mg once a day (typical dosage strengths are 1.5, 3, 4.5 and 6 mg).

Glipizide is usually given in doses from 2.5 to 40 mg once (or twice) a day (typical dosage strengths are 5 and 10 mg), or extended-release glibenclamide in doses from 5 to 20 mg once a day (typical dosage strengths are 2.5, 5 and 10 mg).

Glimepiride is usually given in doses from 1 to 8 mg once a day (typical dosage strengths are 1, 2 and 4 mg).

A dual combination of glibenclamide/metformin is usually given in doses from 1.25/250 once daily to 10/1000 mg twice daily.

A dual combination of glipizide/metformin is usually given in doses from 2.5/250 to 10/1000 mg twice daily.

A dual combination of glimepiride/metformin is usually given in doses from 1/250 to 4/1000 mg twice daily.

A dual combination of rosiglitazone/glimepiride is usually given in doses from 4/1 once or twice daily to 4/2 mg twice daily.

A dual combination of pioglitazone/glimepiride is usually given in doses from 30/2 to 30/4 mg once daily.

A dual combination of rosiglitazone/metformin is usually given in doses from 1/500 to 4/1000 mg twice daily.

A dual combination of pioglitazone/metformin is usually given in doses from 15/500 once or twice daily to 15/850 mg thrice daily.

The non-sulphonylurea insulin secretagogue nateglinide is usually given in doses from 60 to 120 mg with meals; repaglinide is usually given in doses from 0.5 to 4 mg with meals.

Acarbose is usually given in doses from 25 to 100 mg with meals. Miglitol is usually given in doses from 25 to 100 mg with meals.

Examples of combination partners that lower the lipid level in the blood are HMG-CoA-reductase inhibitors such as simvastatin, atorvastatin, lovastatin, fluvastatin, pravastatin and rosuvastatin; fibrates such as bezafibrate, fenofibrate, clofibrate, gemfibrozil, etofibrate and etofyllinclofibrate; nicotinic acid and the derivatives thereof such as acipimox; PPAR-alpha agonists; PPAR-delta agonists; inhibitors of acyl-coenzyme A:cholesterolacyltransferase (ACAT; EC 2.3.1.26) such as avasimibe; cholesterol resorption inhibitors such as ezetimib; substances that bind to bile acid, such as cholestyramine, colestipol and colesevelam; inhibitors of bile acid transport; HDL modulating active substances such as D4F, reverse D4F, LXR modulating active substances and FXR modulating active substances; CETP inhibitors such as torcetrapib, JTT-705 or compound 12 from WO 2007/005572; LDL receptor modulators; and ApoB100 antisense RNA.

A dosage of atorvastatin is usually from 1 mg to 40 mg or 10 mg to 80 mg once a day Examples of combination partners that lower blood pressure are beta-blockers such as atenolol, bisoprolol, celiprolol, metoprolol and carvedilol; diuretics such as hydrochlorothiazide, chlortalidon, xipamide, furosemide, piretanide, torasemide, spironolactone, eplerenone, amiloride and triamterene; calcium channel blockers such as amlodipine, nifedipine, nitrendipine, nisoldipine, nicardipine, felodipine, lacidipine, lercanipidine, manidipine, isradipine, nilvadipine, verapamil, gallopamil and diltiazem; ACE inhibitors such as ramipril, lisinopril, cilazapril, quinapril, captopril, enalapril, benazepril, perindopril, fosinopril and trandolapril; as well as angiotensin II receptor blockers (ARBs) such as telmisartan, candesartan, valsartan, losartan, irbesartan, olmesartan and eprosartan.

A dosage of telmisartan is usually from 20 mg to 320 mg or 40 mg to 160 mg per day.

Examples of combination partners which increase the HDL level in the blood are Cholesteryl Ester Transfer Protein (CETP) inhibitors; inhibitors of endothelial lipase; regulators of ABC1; LXRalpha antagonists; LXRbeta agonists; PPAR-delta agonists; LXRalpha/beta regulators, and substances that increase the expression and/or plasma concentration of apolipoprotein A-I.

Examples of combination partners for the treatment of obesity are sibutramine; tetrahydrolipstatin (orlistat); alizyme; dexfenfluramine; axokine; cannabinoid receptor 1 antagonists such as the CB1 antagonist rimonobant; MCH-1 receptor antagonists; MC4 receptor agonists; NPY5 as well as NPY2 antagonists; beta3-AR agonists such as SB-418790 and AD-9677; 5HT2c receptor agonists such as APD 356; myostatin inhibitors; Acrp30 and adiponectin; steroyl CoA desaturase (SCD1) inhibitors; fatty acid synthase (FAS) inhibitors; CCK receptor agonists; Ghrelin receptor modulators; Pyy 3-36; orexin receptor antagonists; and tesofensine.

Examples of combination partners for the treatment of atherosclerosis are phospholipase A2 inhibitors; inhibitors of tyrosine-kinases (50 mg to 600 mg) such as PDGF-receptor-kinase (cf. EP-A-564409, WO 98/35958, U.S. Pat. No. 5,093,330, WO 2004/005281, and WO 2006/041976); oxLDL antibodies and oxLDL vaccines; apoA-1 Milano; ASA; and VCAM-1 inhibitors.

It is to be understood that the other active substances mentioned herein as combination partners of the salts of this invention also comprise their pharmaceutically acceptable salts as well as hydrates, solvates and polymorphic forms thereof.

The present invention is not to be limited in scope by the specific embodiments described herein. Various modifications of the invention in addition to those described herein may become apparent to those skilled in the art from the present disclosure. Such modifications are intended to fall within the scope of the appended claims.

For avoidance of any doubt, the disclosure of each of the documents and patent applications cited herein is specifically incorporated herein by reference in its entirety.

Further embodiments, features and advantages of the present invention may become apparent from the following examples. The following examples serve to illustrate, by way of example, the principles of the invention without restricting it.

EXAMPLES

Synthesis/Preparation 0.5 g of the free base of BI 1356 are suspended at room temperature in 4 ml of EtOH. The suspension is heated under reflux until a clear solution is obtained which typically is obtained after a few minutes. 1 mol equivalent of the respective acid (see Table 1), either dissolved in EtOH or water is added to the hot solution of BI 1356. Afterwards heating is removed and the solution is slowly cooled down and stored over night at room temperature. In case precipitation is observed, the obtained crystals are removed by filtering and afterwards dried over night at ambient conditions. In case no precipitation was observed the solution is evaporated partially (by approx. 50%) and than stored for another night in the refrigerator (4° C.). Precipitated crystals are also removed by filtering and afterwards dried over night at ambient conditions. The obtained crystals are analysed by polarized light microscopy, X-ray powder diffraction and thermal analysis.

Used Equipment for X-Ray Powder Diffraction Measurements:

STOE Stadi P X-ray powder diffractometer with a position sensitive detector working in transmission mode with a curved Germanium (111) primary monochromator; used wavelength: $CuK_{\alpha 1}$ mit $\lambda=1.540598$ Å; power settings of X-ray tube: 40 kV, 40 mA; 2 Θ -range: 3-40°

For indexing of the X-ray powder patterns where single crystal structure data is available the program TREOR was used which is part of the STOE Stadi P software package. Tables 2-13 show the characteristic X-ray peaks including normalised intensities up to 30° in 2 Θ. The respective XRPD-diagrams are shown in FIGS. 1-12 in the appendix.

Used Equipment for Thermoanalysis:

A DSC 822 from Fa. Mettler Toldeo was used. The following standard parameters were applied: heating rate: 10 K/min; crucible type: pin-holed aluminium crucible; atmosphere: $N_2$, 80 ml/min flow rate; typical weight-in quantities: 3-10 mg.

A TGA/SDTA 851 from Mettler Toledo coupled with a Nicolet FT-IR 4700 spectrometer was used (for analysis of volatile material). The following standard parameters were applied: heating rate: 10 K/min; crucible type: open aluminium oxide crucible; atmosphere: $N_2$, 20 ml/min flow rate; typical weight-in quantities: 15-25 mg.

The melting point ($=T_{fus}$) measured by DSC is given in Table 1.

TABLE 1

Salt formation of BI 1356

Figure 2:
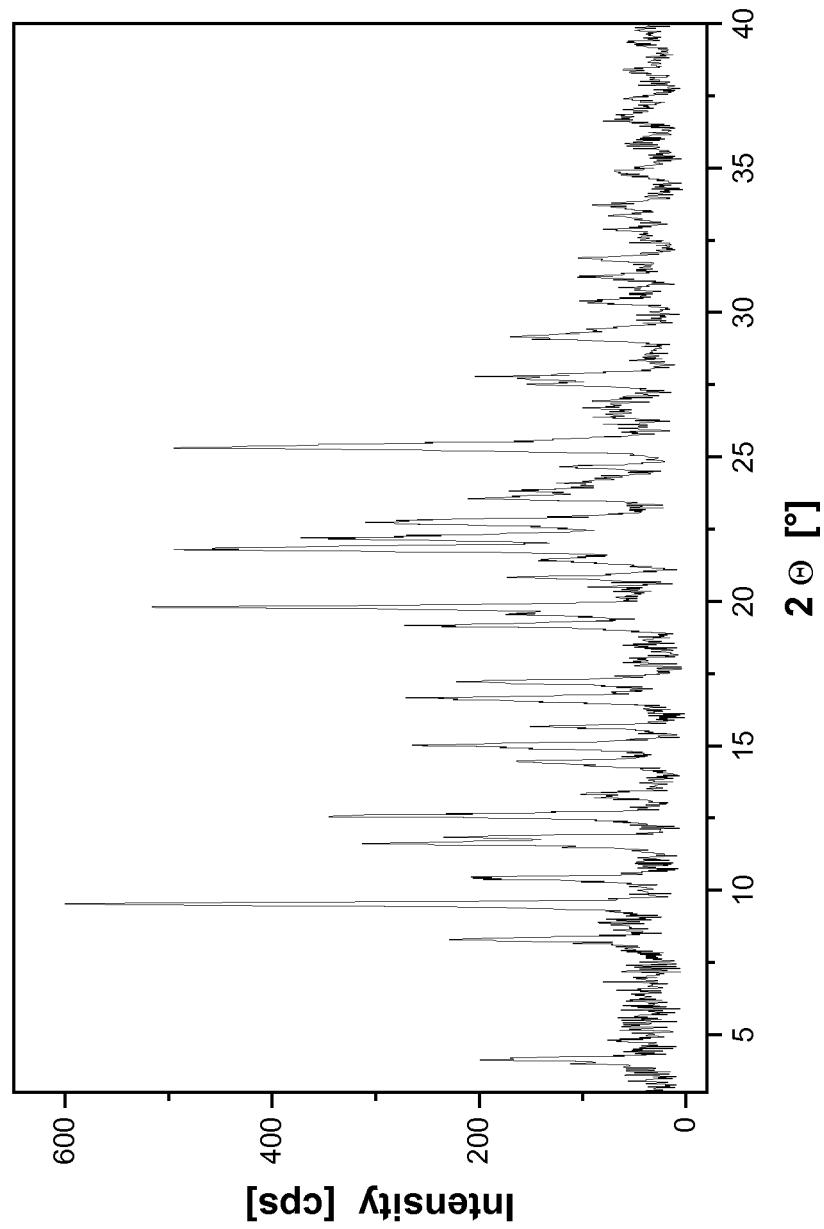
FIG. 2 shows the XRPD diagram of the bromide salt of BI 1356.
Figure 3:
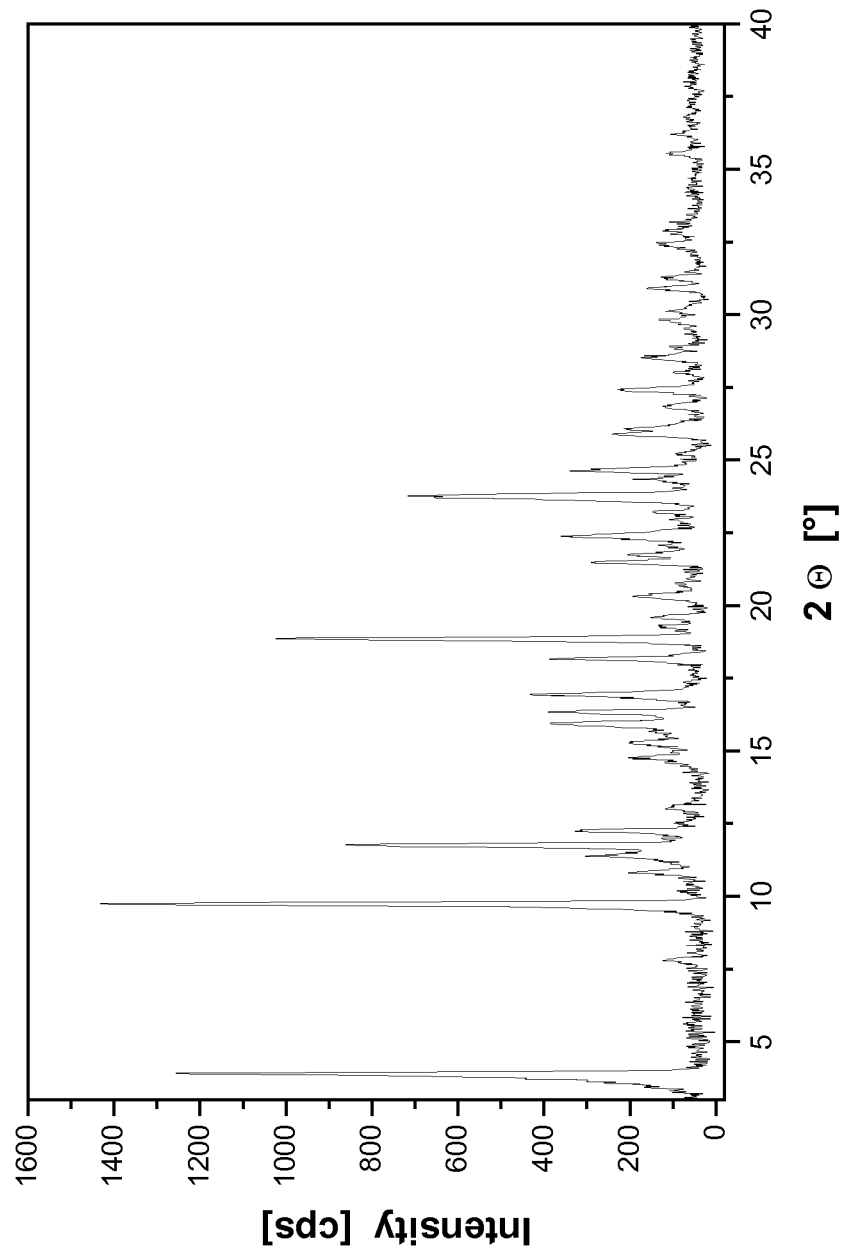
FIG. 3 shows the XRPD diagram of the benzoate salt of BI 1356.
Figure 4:
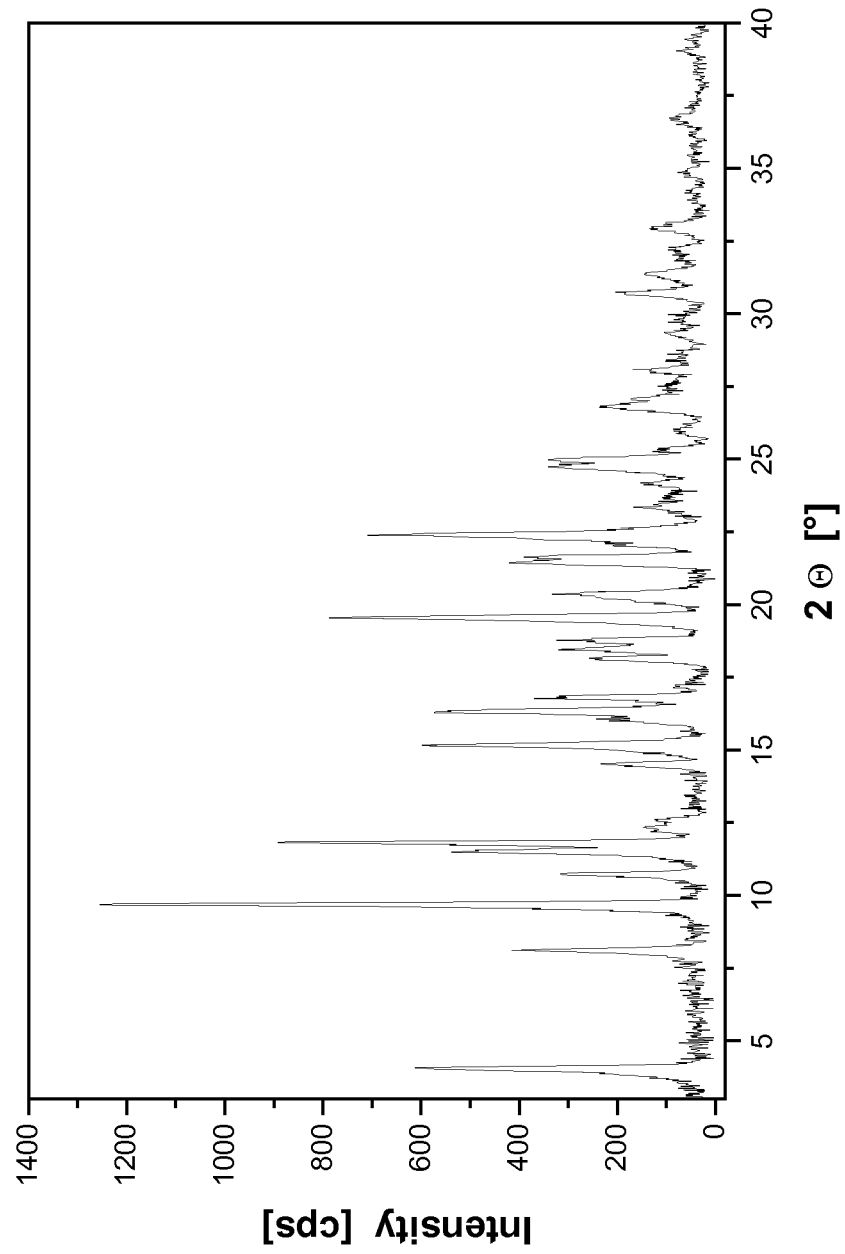
FIG. 4 shows the XRPD diagram of the eslylate salt of BI 1356.
Figure 5:
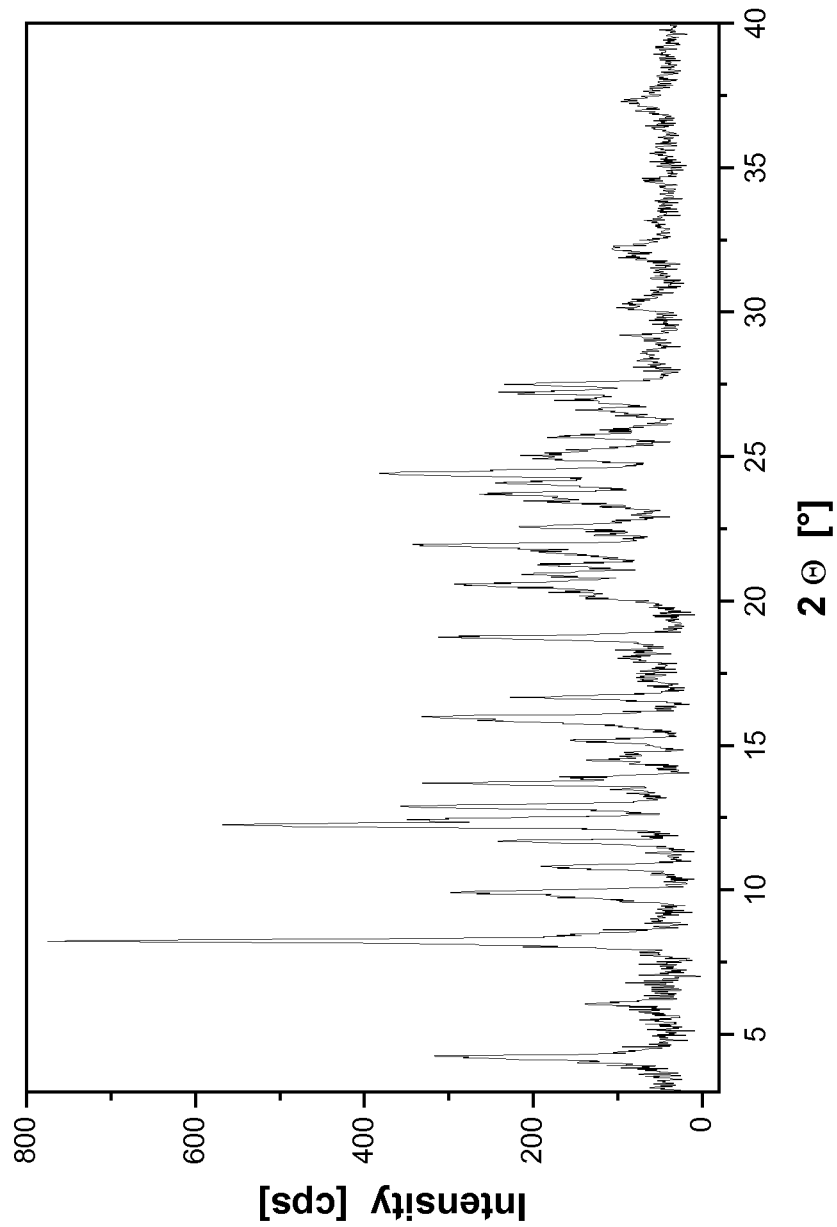
FIG. 5 shows the XRPD diagram of the fumarate salt of BI 1356.
Figure 6:
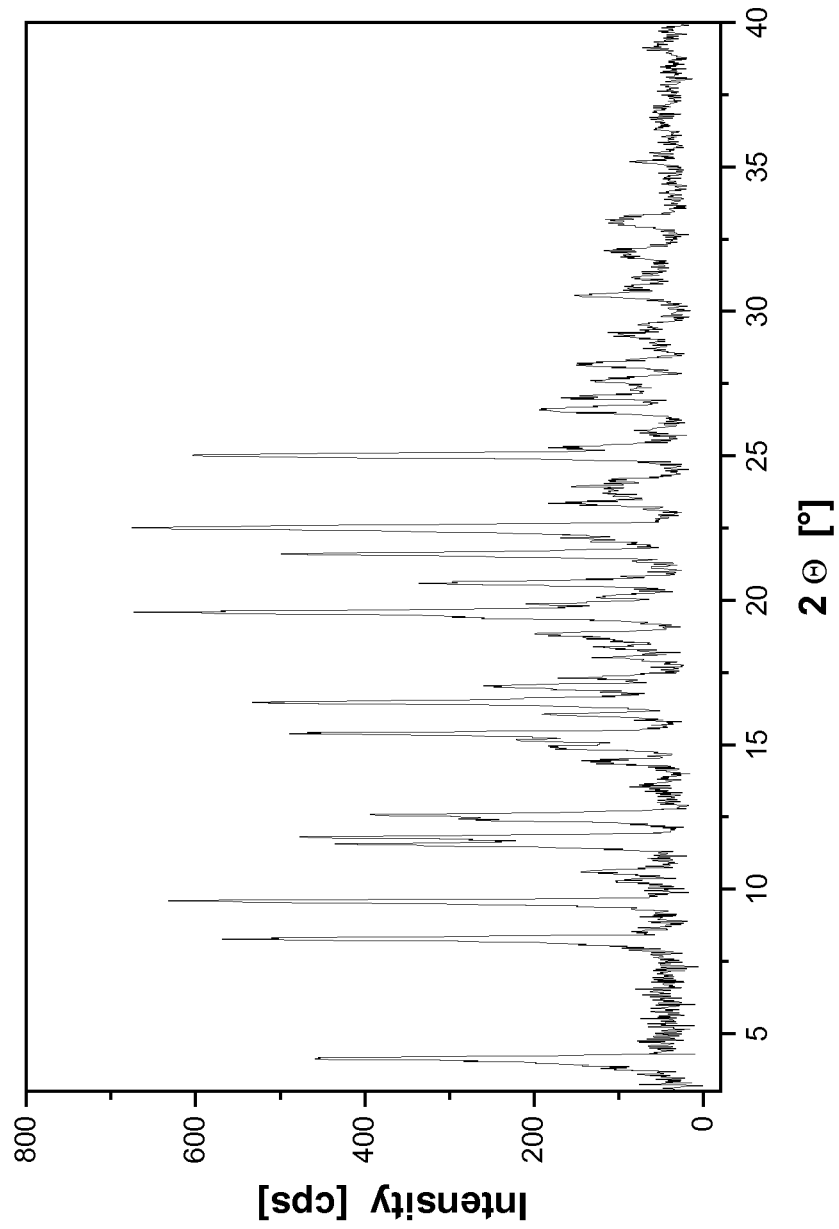
FIG. 6 shows the XRPD diagram of the mesylate salt of BI 1356.
Figure 7:
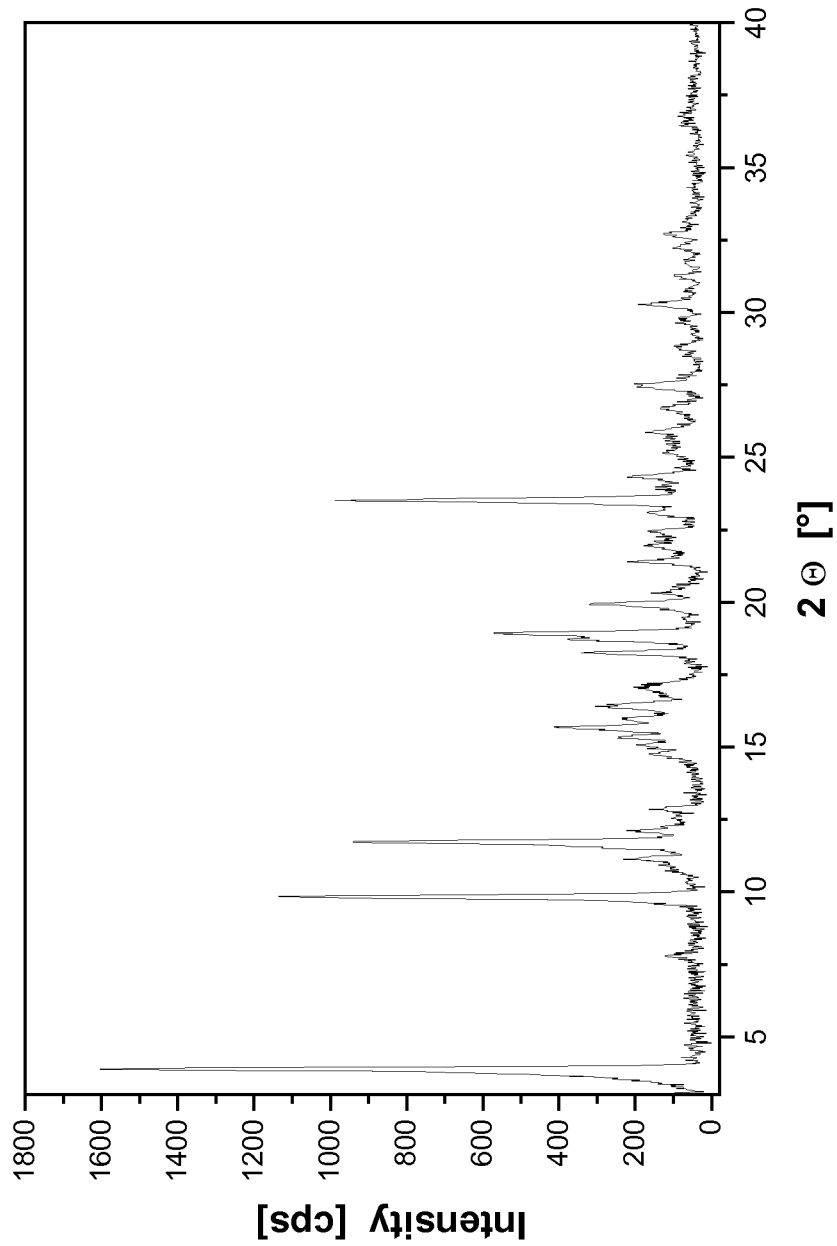
FIG. 7 shows the XRPD diagram of the salicylate salt of BI 1356.
Figure 8:
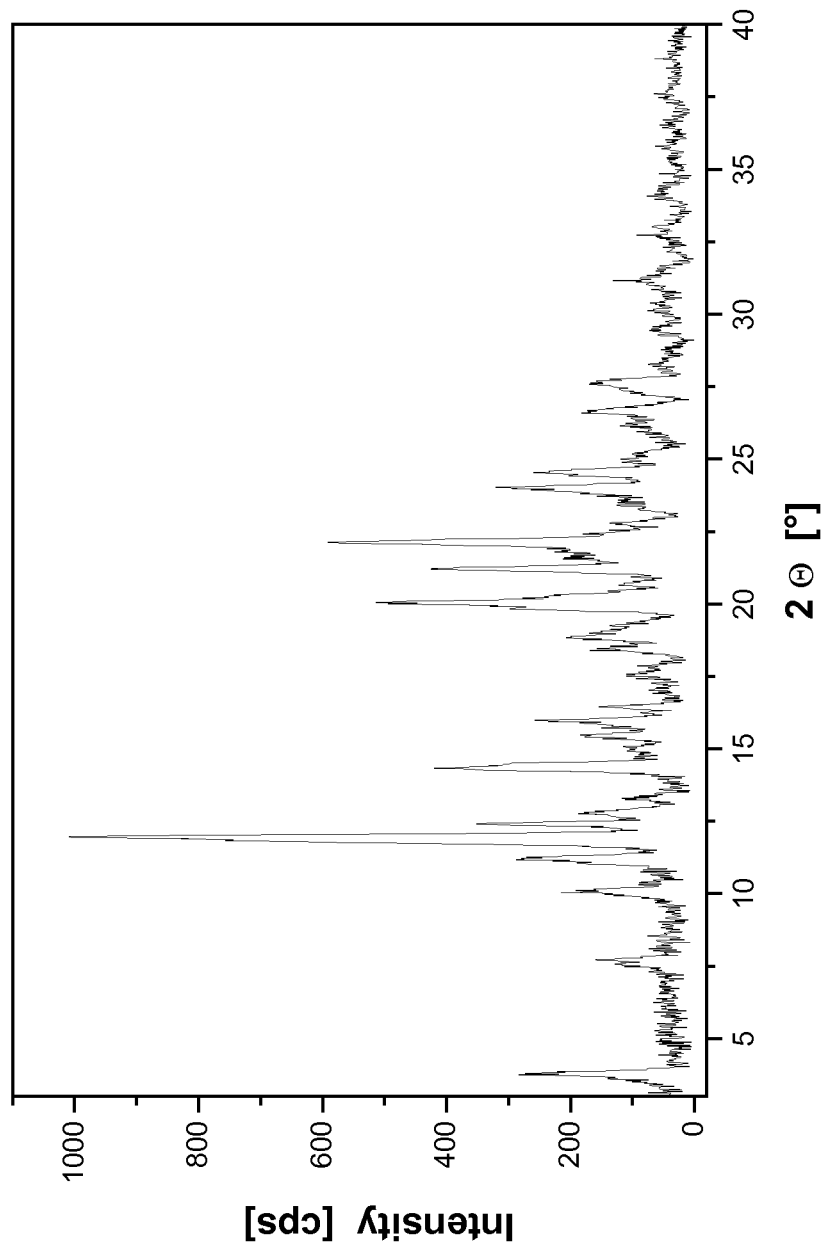
FIG. 8 shows the XRPD diagram of the tosylate salt of BI 1356.

| salt form (used acid) | stoichiometry base:c.i. | thermal analysis (m.p.) | XRPD-data |
|---|---|---|---|
| besylate (benzenesulfonic acid) | 1:1 | $T_{fus}$: ca. 175° C. | see Tab. 2 & FIG. 1 |
| bromide (hydrobromic acid) | 1:1 | $T_{fus}$: ca. 175° C. | see Tab. 3 & FIG. 2 |
| benzoate (benzoic acid) | 1:1 | $T_{fus}$: ca. 155° C. | see Tab. 4 & FIG. 3 |
| esylate (ethanesulfonic acid) | 1:1 | $T_{fus}$: ca. 190° C. | see Tab. 5 & FIG. 4 |
| fumarate (fumaric acid) | 1:1 | $T_{fus}$: ca. 225° C. | see Tab. 6 & FIG. 5 |
| mesylate (methanesulfonic acid) | 1:1 | $T_{fus}$: ca. 160° C. | see Tab. 7 & FIG. 6 |
| salicylate (salicylic acid) | 1:1 | $T_{fus}$: ca. 165° C. | see Tab. 8 & FIG. 7 |
| tosylate (p-toluenesulfonic acid) | 1:1 | $T_{fus}$: ca. 160° C. | see Tab. 9 & FIG. 8 |
| chloride (hydrochloric acid) | 1:1 | $T_{fus}$: ca. 175° C. | see Tab. 10 & FIG. 9 |
| glyoclate (glycolic acid) | 1:1 | $T_{fus}$: ca. 165° C. | see Tab. 11 & FIG. 10 |
| malonate (malonic acid) | 1:1 | $T_{fus}$: ca. 100° C. | see Tab. 12 & FIG. 11 |
| gentisate (2,5-dihydroxybenzoic acid) | 1:1 | $T_{fus}$: ca. 170° C. | see Tab. 13 & FIG. 12 |

TABLE 2

X-ray diffraction peaks (up to 30° 2 Θ) including normalised intensities of the besylate salt of BI 1356

| 2 Θ [°] | $d_{hkl}$ [Å] | $I/I_o$ |
|---|---|---|
| 3.95 | 22.37 | 41 |
| 7.35 | 12.02 | 12 |
| 7.86 | 11.24 | 37 |
| 9.73 | 9.09 | 67 |
| 10.95 | 8.07 | 15 |
| 11.95 | 7.40 | 100 |
| 13.18 | 6.71 | 14 |
| 14.71 | 6.02 | 16 |
| 15.12 | 5.85 | 46 |
| 15.49 | 5.71 | 50 |
| 17.38 | 5.10 | 16 |
| 18.25 | 4.86 | 26 |
| 19.01 | 4.66 | 81 |
| 19.95 | 4.45 | 19 |
| 21.49 | 4.13 | 27 |
| 22.59 | 3.93 | 52 |
| 23.15 | 3.84 | 25 |
| 24.16 | 3.68 | 16 |
| 25.71 | 3.46 | 22 |
| 26.60 | 3.35 | 14 |
| 27.32 | 3.26 | 15 |
| 28.44 | 3.14 | 6 |
| 29.60 | 3.02 | 6 |

TABLE 3

X-ray diffraction peaks (up to 30° 2 Θ) including normalised intensities of the bromide salt of BI 1356

| 2 Θ [°] | $d_{hkl}$ [Å] | $I/I_o$ |
|---|---|---|
| 4.14 | 21.31 | 29 |
| 8.31 | 10.63 | 36 |
| 9.53 | 9.27 | 100 |
| 10.43 | 8.48 | 31 |
| 11.62 | 7.61 | 49 |
| 11.83 | 7.47 | 32 |
| 12.58 | 7.03 | 58 |
| 13.31 | 6.64 | 9 |
| 14.45 | 6.13 | 24 |
| 15.03 | 5.89 | 42 |
| 15.67 | 5.65 | 23 |
| 16.66 | 5.32 | 41 |
| 17.23 | 5.14 | 34 |
| 19.17 | 4.63 | 41 |
| 19.57 | 4.53 | 23 |
| 19.80 | 4.48 | 88 |
| 20.84 | 4.26 | 27 |
| 21.43 | 4.14 | 20 |
| 21.82 | 4.07 | 83 |
| 22.19 | 4.00 | 56 |
| 22.75 | 3.91 | 48 |
| 23.57 | 3.77 | 33 |
| 23.84 | 3.73 | 27 |
| 24.10 | 3.69 | 19 |
| 24.67 | 3.61 | 17 |
| 25.32 | 3.51 | 84 |
| 27.51 | 3.24 | 23 |
| 27.78 | 3.21 | 29 |
| 29.17 | 3.06 | 26 |

TABLE 4

X-ray diffraction peaks (up to 30° 2Θ) including normalised intensities of the benzoate salt of BI 1356

| 2Θ [°] | $d_{hkl}$ [Å] | I/I$_o$ |
|---|---|---|
| 3.91 | 22.56 | 88 |
| 7.82 | 11.30 | 6 |
| 9.75 | 9.06 | 100 |
| 10.84 | 8.16 | 11 |
| 11.38 | 7.77 | 19 |
| 11.76 | 7.52 | 59 |
| 12.26 | 7.22 | 22 |
| 13.04 | 6.78 | 6 |
| 14.76 | 6.00 | 11 |
| 15.29 | 5.79 | 12 |
| 15.94 | 5.56 | 25 |
| 16.35 | 5.42 | 25 |
| 16.95 | 5.23 | 28 |
| 18.17 | 4.88 | 25 |
| 18.86 | 4.70 | 71 |
| 19.28 | 4.60 | 7 |
| 19.60 | 4.53 | 8 |
| 20.32 | 4.37 | 12 |
| 21.49 | 4.13 | 19 |
| 21.76 | 4.08 | 11 |
| 22.07 | 4.02 | 6 |
| 22.40 | 3.97 | 23 |
| 23.23 | 3.83 | 8 |
| 23.76 | 3.74 | 47 |
| 24.34 | 3.65 | 10 |
| 24.64 | 3.61 | 21 |
| 25.22 | 3.53 | 3 |
| 25.90 | 3.44 | 15 |
| 26.07 | 3.42 | 13 |
| 26.85 | 3.32 | 6 |
| 27.43 | 3.25 | 14 |
| 28.02 | 3.18 | 5 |
| 28.52 | 3.13 | 10 |
| 28.87 | 3.09 | 4 |
| 29.84 | 2.99 | 8 |

TABLE 5

X-ray diffraction peaks (up to 30° 2Θ) including normalised intensities of the esylate salt of BI 1356

| 2Θ [°] | $d_{hkl}$ [Å] | I/I$_o$ |
|---|---|---|
| 4.06 | 21.75 | 46 |
| 8.12 | 10.87 | 30 |
| 9.70 | 9.11 | 100 |
| 10.74 | 8.23 | 24 |
| 11.51 | 7.68 | 40 |
| 11.83 | 7.48 | 69 |
| 12.35 | 7.16 | 10 |
| 12.59 | 7.03 | 8 |
| 14.52 | 6.09 | 17 |
| 15.17 | 5.83 | 46 |
| 16.07 | 5.51 | 15 |
| 16.32 | 5.43 | 44 |
| 16.79 | 5.28 | 26 |
| 18.15 | 4.88 | 18 |
| 18.47 | 4.80 | 23 |
| 18.78 | 4.72 | 21 |
| 19.56 | 4.53 | 60 |
| 20.37 | 4.36 | 23 |
| 21.45 | 4.14 | 32 |
| 21.64 | 4.10 | 28 |
| 22.41 | 3.96 | 53 |
| 23.35 | 3.81 | 10 |
| 24.19 | 3.68 | 9 |
| 24.76 | 3.59 | 24 |
| 24.98 | 3.56 | 25 |
| 25.30 | 3.52 | 8 |
| 25.99 | 3.43 | 5 |
| 26.83 | 3.32 | 17 |
| 27.08 | 3.29 | 12 |
| 28.10 | 3.17 | 10 |
| 29.32 | 3.04 | 5 |

TABLE 6

X-ray diffraction peaks (up to 30° 2Θ) including normalised intensities of the fumarate salt of BI 1356

| 2Θ [°] | $d_{hkl}$ [Å] | I/I$_o$ |
|---|---|---|
| 4.23 | 20.86 | 36 |
| 6.06 | 14.58 | 15 |
| 8.24 | 10.72 | 100 |
| 9.92 | 8.91 | 34 |
| 10.82 | 8.17 | 21 |
| 11.69 | 7.56 | 28 |
| 12.26 | 7.22 | 70 |
| 12.43 | 7.12 | 39 |
| 12.89 | 6.86 | 43 |
| 13.70 | 6.46 | 36 |
| 13.87 | 6.38 | 15 |
| 14.50 | 6.10 | 13 |
| 15.19 | 5.83 | 17 |
| 15.98 | 5.54 | 39 |
| 16.67 | 5.31 | 25 |
| 18.75 | 4.73 | 37 |
| 20.16 | 4.40 | 13 |
| 20.30 | 4.37 | 20 |
| 20.58 | 4.31 | 32 |
| 20.93 | 4.24 | 24 |
| 21.25 | 4.18 | 20 |
| 21.93 | 4.05 | 40 |
| 22.57 | 3.94 | 24 |
| 23.47 | 3.79 | 21 |
| 23.71 | 3.75 | 30 |
| 24.09 | 3.69 | 28 |
| 24.42 | 3.64 | 46 |
| 25.04 | 3.55 | 22 |
| 25.67 | 3.47 | 19 |
| 25.90 | 3.44 | 7 |
| 26.62 | 3.35 | 14 |
| 26.94 | 3.31 | 16 |
| 27.22 | 3.27 | 25 |
| 27.50 | 3.24 | 25 |
| 29.19 | 3.06 | 7 |

TABLE 7

X-ray diffraction peaks (up to 30° 2Θ) including normalised intensities of the mesylate salt of BI 1356

| 2Θ [°] | $d_{hkl}$ [Å] | I/I$_o$ |
|---|---|---|
| 4.15 | 21.29 | 71 |
| 8.29 | 10.66 | 83 |
| 9.59 | 9.22 | 93 |
| 10.59 | 8.35 | 12 |
| 11.56 | 7.65 | 66 |
| 11.80 | 7.49 | 70 |
| 12.42 | 7.12 | 39 |
| 12.57 | 7.03 | 56 |
| 14.45 | 6.12 | 17 |
| 14.91 | 5.94 | 25 |
| 15.16 | 5.84 | 31 |
| 15.40 | 5.75 | 72 |

TABLE 7-continued

X-ray diffraction peaks (up to 30° 2 Θ) including normalised intensities of the mesylate salt of BI 1356

| 2 Θ [°] | $d_{hkl}$ [Å] | I/I$_o$ |
|---|---|---|
| 16.05 | 5.52 | 26 |
| 16.47 | 5.38 | 80 |
| 17.03 | 5.20 | 35 |
| 17.32 | 5.12 | 19 |
| 18.02 | 4.92 | 15 |
| 18.38 | 4.82 | 15 |
| 18.83 | 4.71 | 27 |
| 19.58 | 4.53 | 98 |
| 19.87 | 4.46 | 27 |
| 20.14 | 4.41 | 14 |
| 20.61 | 4.31 | 46 |
| 21.61 | 4.11 | 75 |
| 22.15 | 4.01 | 20 |
| 22.51 | 3.95 | 100 |
| 23.38 | 3.80 | 22 |
| 23.72 | 3.75 | 15 |
| 23.96 | 3.71 | 20 |
| 24.16 | 3.68 | 14 |
| 25.02 | 3.56 | 93 |
| 25.29 | 3.52 | 25 |
| 26.60 | 3.35 | 27 |
| 27.01 | 3.30 | 17 |
| 27.60 | 3.23 | 16 |
| 28.15 | 3.17 | 20 |
| 29.20 | 3.06 | 11 |

TABLE 8

X-ray diffraction peaks (up to 30° 2 Θ) including normalised intensities of salicylate salt of BI 1356

| 2 Θ [°] | $d_{hkl}$ [Å] | I/I$_o$ |
|---|---|---|
| 3.91 | 22.61 | 100 |
| 7.79 | 11.33 | 6 |
| 9.85 | 8.97 | 69 |
| 11.15 | 7.93 | 12 |
| 11.74 | 7.53 | 59 |
| 12.12 | 7.30 | 12 |
| 12.86 | 6.88 | 7 |
| 14.77 | 5.99 | 8 |
| 15.08 | 5.87 | 11 |
| 15.32 | 5.78 | 14 |
| 15.69 | 5.64 | 23 |
| 15.98 | 5.54 | 12 |
| 16.42 | 5.39 | 16 |
| 17.05 | 5.20 | 10 |
| 18.27 | 4.85 | 20 |
| 18.74 | 4.73 | 23 |
| 18.92 | 4.69 | 34 |
| 19.95 | 4.45 | 18 |
| 20.32 | 4.37 | 7 |
| 21.41 | 4.15 | 12 |
| 21.96 | 4.04 | 9 |
| 22.46 | 3.96 | 8 |
| 23.10 | 3.85 | 8 |
| 23.52 | 3.78 | 62 |
| 24.34 | 3.65 | 11 |
| 25.16 | 3.54 | 6 |
| 25.87 | 3.44 | 9 |
| 26.69 | 3.34 | 7 |
| 27.50 | 3.24 | 10 |
| 28.85 | 3.09 | 4 |
| 29.69 | 3.01 | 3 |
| 30.28 | 2.95 | 10 |

TABLE 9

X-ray diffraction peaks (up to 30° 2 Θ) including normalised intensities of tosylate salt of BI 1356

| 2 Θ [°] | $d_{hkl}$ [Å] | I/I$_o$ |
|---|---|---|
| 3.79 | 23.32 | 25 |
| 7.58 | 11.66 | 10 |
| 7.74 | 11.42 | 14 |
| 10.05 | 8.79 | 18 |
| 11.20 | 7.89 | 27 |
| 11.96 | 7.39 | 100 |
| 12.42 | 7.12 | 33 |
| 12.79 | 6.92 | 16 |
| 13.34 | 6.63 | 7 |
| 14.34 | 6.17 | 39 |
| 15.47 | 5.72 | 16 |
| 15.99 | 5.54 | 23 |
| 16.46 | 5.38 | 13 |
| 17.55 | 5.05 | 8 |
| 18.47 | 4.80 | 12 |
| 18.85 | 4.70 | 20 |
| 20.05 | 4.42 | 50 |
| 21.22 | 4.18 | 43 |
| 21.61 | 4.11 | 19 |
| 22.14 | 4.01 | 59 |
| 22.79 | 3.90 | 10 |
| 23.42 | 3.80 | 10 |
| 24.03 | 3.70 | 29 |
| 24.55 | 3.62 | 24 |
| 26.62 | 3.35 | 16 |
| 27.62 | 3.23 | 15 |

TABLE 10

Indexed X-ray diffraction peaks (up to 30° 2 Θ) including normalised intensities of the tetrahydrate of the hydrochloride of BI 1356

| 2 Θ [°] | $d_{hkl}$ [Å] | I/I$_o$ | h | k | l | 2 Θ$_{obs}$ − 2 Θ$_{calc}$ [°] |
|---|---|---|---|---|---|---|
| 4.52 | 19.55 | 43 | 0 | 0 | 1 | 0.002 |
| 9.86 | 8.97 | 100 | 2 | 0 | 0 | −0.002 |
| 10.56 | 8.37 | 7 | −2 | 0 | 1 | 0.001 |
| 11.60 | 7.62 | 70 | 0 | 1 | 1 | 0.011 |
| 11.77 | 7.52 | 64 | 1 | 1 | 0 | 0.005 |
| 12.49 | 7.08 | 92 | −1 | 1 | 1 | 0.006 |
| 12.72 | 6.95 | 13 | 1 | 1 | 1 | −0.005 |
| 13.83 | 6.40 | 58 | 2 | 0 | 2 | −0.007 |
| 15.04 | 5.89 | 56 | −2 | 1 | 1 | 0.005 |
| 15.43 | 5.74 | 41 | 2 | 1 | 1 | −0.006 |
| 16.78 | 5.28 | 6 | −2 | 1 | 2 | −0.009 |
| 17.50 | 5.06 | 42 | 2 | 1 | 2 | −0.006 |
| 18.28 | 4.85 | 6 | 1 | 1 | 3 | 0.028 |
| 19.08 | 4.65 | 47 | 3 | 1 | 1 | −0.008 |
| 19.47 | 4.56 | 17 | −3 | 0 | 3 | 0.036 |
| 20.00 | 4.44 | 27 | −3 | 1 | 2 | 0.029 |
| 20.61 | 4.31 | 8 | 4 | 0 | 1 | −0.002 |
| 20.90 | 4.25 | 16 | 3 | 1 | 2 | 0.017 |
| 21.44 | 4.14 | 29 | 0 | 2 | 0 | −0.003 |
| 22.01 | 4.04 | 49 | 1 | 2 | 0 | −0.003 |
| 22.37 | 3.97 | 96 | 4 | 0 | 2 | 0.013 |
| 22.78 | 3.90 | 16 | −2 | 1 | 4 | −0.002 |
| 23.44 | 3.79 | 35 | 3 | 1 | 3 | −0.010 |
| 23.95 | 3.71 | 12 | −2 | 2 | 1 | −0.010 |
| 24.22 | 3.67 | 10 | 2 | 2 | 1 | <0.001 |
| 24.82 | 3.58 | 61 | 5 | 0 | 0 | 0.017 |
| 25.12 | 3.54 | 78 | −2 | 2 | 2 | 0.004 |
| 25.64 | 3.47 | 27 | 2 | 2 | 2 | 0.033 |
| 26.13 | 3.41 | 7 | 1 | 2 | 3 | 0.004 |
| 26.38 | 3.38 | 18 | −3 | 0 | 5 | 0.040 |
| 27.38 | 3.25 | 20 | −3 | 2 | 2 | 0.001 |
| 27.75 | 3.21 | 25 | 5 | 1 | 1 | <0.001 |
| 28.47 | 3.13 | 22 | −1 | 2 | 4 | 0.036 |

TABLE 10-continued

Indexed X-ray diffraction peaks (up to 30° 2 Θ) including normalised intensities of the tetrahydrate of the hydrochloride of BI 1356

| 2 Θ [°] | $d_{hkl}$ [Å] | I/I$_o$ | Indexing h | k | l | 2 Θ$_{obs}$ − 2 Θ$_{calc}$ [°] |
|---|---|---|---|---|---|---|
| 29.14 | 3.06 | 16 | 5 | 1 | 2 | −0.006 |
| 29.49 | 3.03 | 20 | −4 | 2 | 1 | 0.008 |

Indexing is possible with a monoclinic cell, space group P21, with the following lattice parameters: a = 17.974(4) Å, b = 8.282(3) Å, c = 19.607(6), β = 93.9(2)°, V = 2912(2) Å3. All 35 peaks can be indexed with a figure of merit of 42.1

TABLE 11

X-ray diffraction peaks (up to 30° 2 Θ) including normalised intensities of glycolate salt of BI 1356

| 2 Θ [°] | $d_{hkl}$ [Å] | I/I$_o$ |
|---|---|---|
| 3.16 | 27.94 | 18 |
| 5.54 | 15.95 | 4 |
| 6.35 | 13.90 | 100 |
| 8.41 | 10.51 | 31 |
| 9.55 | 9.25 | 15 |
| 11.05 | 8.00 | 5 |
| 11.48 | 7.70 | 26 |
| 13.88 | 6.37 | 13 |
| 15.94 | 5.56 | 14 |
| 17.81 | 4.98 | 2 |
| 18.11 | 4.90 | 2 |
| 18.96 | 4.68 | 4 |
| 19.45 | 4.56 | 4 |
| 19.95 | 4.45 | 10 |
| 21.01 | 4.22 | 29 |
| 21.97 | 4.04 | 3 |
| 22.67 | 3.92 | 26 |
| 23.12 | 3.84 | 14 |
| 24.01 | 3.70 | 2 |
| 24.63 | 3.61 | 2 |
| 25.27 | 3.52 | 7 |
| 26.49 | 3.36 | 8 |
| 26.88 | 3.31 | 13 |
| 27.65 | 3.22 | 7 |
| 28.75 | 3.10 | 1 |
| 29.44 | 3.03 | 2 |
| 30.21 | 2.96 | 1 |

TABLE 12

X-ray diffraction peaks (up to 30° 2 Θ) including normalised intensities of malonate salt of BI 1356

| 2 Θ [°] | $d_{hkl}$ [Å] | I/I$_o$ |
|---|---|---|
| 4.14 | 21.34 | 62 |
| 7.96 | 11.10 | 11 |
| 8.30 | 10.65 | 40 |
| 9.67 | 9.14 | 51 |
| 10.14 | 8.72 | 5 |
| 10.39 | 8.50 | 10 |
| 11.48 | 7.70 | 39 |
| 11.76 | 7.52 | 35 |
| 11.97 | 7.39 | 15 |
| 12.52 | 7.06 | 100 |
| 13.54 | 6.53 | 5 |
| 14.45 | 6.12 | 11 |
| 14.97 | 5.91 | 19 |
| 15.10 | 5.86 | 16 |
| 15.52 | 5.71 | 35 |
| 16.07 | 5.51 | 4 |
| 16.50 | 5.37 | 54 |
| 17.01 | 5.21 | 14 |
| 17.28 | 5.13 | 19 |

TABLE 12-continued

X-ray diffraction peaks (up to 30° 2 Θ) including normalised intensities of malonate salt of BI 1356

| 2 Θ [°] | $d_{hkl}$ [Å] | I/I$_o$ |
|---|---|---|
| 18.07 | 4.91 | 17 |
| 18.44 | 4.81 | 31 |
| 18.67 | 4.75 | 13 |
| 18.95 | 4.68 | 11 |
| 19.32 | 4.59 | 20 |
| 19.70 | 4.50 | 60 |
| 19.98 | 4.44 | 13 |
| 20.55 | 4.32 | 23 |
| 20.86 | 4.25 | 14 |
| 21.50 | 4.13 | 33 |
| 21.73 | 4.09 | 38 |
| 22.37 | 3.97 | 33 |
| 22.75 | 3.91 | 71 |
| 23.51 | 3.78 | 31 |
| 24.00 | 3.70 | 21 |
| 25.19 | 3.53 | 57 |
| 25.89 | 3.44 | 10 |
| 26.45 | 3.37 | 8 |
| 26.87 | 3.32 | 17 |
| 27.53 | 3.24 | 16 |
| 28.14 | 3.17 | 13 |
| 28.75 | 3.10 | 4 |
| 29.22 | 3.05 | 11 |
| 29.46 | 3.03 | 11 |

TABLE 13

X-ray diffraction peaks (up to 30° 2 Θ) including normalised intensities of gentisate salt of BI 1356

| 2 Θ [°] | $d_{hkl}$ [Å] | I/I$_o$ |
|---|---|---|
| 4.06 | 21.73 | 100 |
| 9.69 | 9.12 | 90 |
| 10.83 | 8.16 | 11 |
| 11.30 | 7.83 | 75 |
| 11.72 | 7.55 | 85 |
| 13.15 | 6.73 | 12 |
| 14.34 | 6.17 | 20 |
| 14.70 | 6.02 | 31 |
| 15.14 | 5.85 | 21 |
| 15.70 | 5.64 | 11 |
| 16.15 | 5.48 | 35 |
| 16.50 | 5.37 | 8 |
| 16.89 | 5.24 | 15 |
| 18.02 | 4.92 | 7 |
| 18.71 | 4.74 | 6 |
| 19.08 | 4.65 | 25 |
| 19.41 | 4.57 | 64 |
| 21.15 | 4.20 | 23 |
| 21.37 | 4.16 | 18 |
| 21.80 | 4.07 | 11 |
| 22.33 | 3.98 | 7 |
| 22.72 | 3.91 | 10 |
| 23.21 | 3.83 | 26 |
| 23.85 | 3.73 | 81 |
| 24.20 | 3.67 | 30 |
| 24.51 | 3.63 | 16 |
| 24.92 | 3.57 | 18 |
| 25.79 | 3.45 | 18 |
| 25.99 | 3.43 | 13 |
| 26.27 | 3.39 | 9 |
| 26.81 | 3.32 | 8 |
| 27.32 | 3.26 | 9 |
| 27.84 | 3.20 | 5 |
| 28.62 | 3.12 | 5 |
| 29.27 | 3.05 | 8 |
| 29.61 | 3.01 | 8 |
| 29.96 | 2.98 | 9 |

The invention claimed is:

1. A salt of 1-[(4-methyl-quinazolin-2-yl)methyl]-3-methyl-7-(2-butyn-1-yl)-8-(3-(R)-amino-piperidin-1-yl)-xanthine and a pharmaceutically acceptable acid in a 1:1 stoichiometry in the form of an organic solvate, hydrate, or mixed hydrate/organic solvate thereof.

2. An acid addition salt of 1-[(4-methyl-quinazolin-2-yl)methyl]-3-methyl-7-(2-butyn-1-yl)-8-(3-(R)-amino-piperidin-1-yl)-xanthine with an acid selected from hydrochloric acid, hydrobromic acid, phosphoric acid, nitric acid, sulfuric acid, acetic acid, 2,2-dichloroacetic acid, adipic acid, D-ascorbic acid, L-ascorbic acid, D-aspartic acid, L-aspartic acid, benzenesulfonic acid, benzoic acid, 4-acetamido-benzoic acid, (+)-camphoric acid, (−)-camphoric acid, (+)-camphor-10-sulfonic, (−)-camphor-10-sulfonic, capric acid (decanoic acid), caproic acid (hexanoic acid), caprylic acid (octanoic acid), carbonic acid, cinnamic acid, citric acid, cyclamic acid, dodecylsulfuric acid, ethane-1,2-disulfonic acid, ethanesulfonic acid, 2-hydroxy-ethanesulfonic acid, formic acid, fumaric acid, galactaric acid, gentisic acid, D-glucoheptonic acid, L-glucoheptonic acid, D-gluconic acid, L-gluconic acid; D-glucuronic acid, L-glucuronic acid, glutamic acid, glutaric acid, 2-oxo-glutaric acid, glycerophosphoric acid, glycolic acid, hippuric acid, isobutyric acid, D-lactic acid, L-lactic acid, lactobionic acid, lauric acid, maleic acid, D-malic acid, L-malic acid, malonic acid, D-mandelic acid, L-mandelic acid, methanesulfonic acid, naphthalene-1,5-disulfonic acid, naphthalene-2-sulfonic acid, 1-hydroxy-2-naphthoic acid, nicotinic acid, oleic acid, orotic acid, oxalic acid, palmitic acid, pamoic acid (embonic acid), propionic acid, D-pyroglutamic acid, L-pyroglutamic acid, salicyclic acid, 4-aminosalicyclic acid, sebacic acid, stearic acid, succinic acid, D-tartaric acid, L-tartaric acid, thiocyanic acid, p-toluenesulfonic acid and undecylenic acid, in the form of an organic solvate, hydrate, or mixed hydrate/organic solvate thereof.

3. The salt according to claim 2, which is selected from the group consisting of a besylate salt, a hydrobromide salt, a benzoate salt, an esylate salt, a fumarate salt, a mesylate salt, a salicylate salt, a tosylate salt, a hydrochloride salt, a glycolate salt, a malonate salt and a gentisate salt.

4. The salt according to claim 2, in the form of a solvate.

5. The salt according to claim 2, in the form of an organic solvate.

6. The salt according to claim 2, in the form of a hydrate.

7. The salt according to claim 2, in the form of a mixed hydrate/organic solvate.

8. The salt according to claim 2, in crystalline, partially crystalline, amorphous or polymorphous form.

9. A pharmaceutical composition comprising a salt according to claim 1, optionally together with one or more pharmaceutically acceptable carriers and/or diluents.

10. The pharmaceutical composition according to claim 9, further comprising one or more other active substances.

* * * * *